United States Patent [19]

Hegarty et al.

[11] 4,032,659
[45] June 28, 1977

[54] METHOD OF VIRAL CHEMOPROPHYLAXIS

[75] Inventors: Charles Paul Hegarty, Radnor; Helen C. Pietryk, Havertown, both of Pa.

[73] Assignee: American Home Products Corporation, New York, N.Y.

[22] Filed: June 26, 1975

[21] Appl. No.: 590,536

Related U.S. Application Data

[62] Division of Ser. No. 808,989, March 20, 1969, abandoned.

[52] U.S. Cl. .............................. 424/323; 424/311; 424/274
[51] Int. Cl.$^2$ .............. A61K 31/175; A61K 31/22; A61K 31/40
[58] Field of Search .................. 424/323, 311, 274

[56] References Cited

OTHER PUBLICATIONS

Usui, Chem. Abst., vol. 70, (1969), p. 76696x.

*Primary Examiner*—Sam Rosen
*Attorney, Agent, or Firm*—Joseph Martin Weigman

[57] ABSTRACT

It has been found that compounds having a stereochemically unencumbered access to a nitrogen-nitrogen bond have antiviral activity in extremely low dose ranges. Hydrazine, hydrazine derivatives and related compounds have been found to be active in protecting animals against disease caused by both DNA and RNA type viruses at doses of about 250 picograms to 250 micrograms per kilogram of host body weight.

10 Claims, No Drawings

METHOD OF VIRAL CHEMOPROPHYLAXIS

CROSS-REFERENCE TO RELATED APPLICATIONS

This application is a division of application Ser. No. 808,989 filed Mar. 20, 1969 and now abandoned.

BACKGROUND OF THE INVENTION

This invention relates to the chemoprophylaxis of disease caused by DNA and RNA viruses. More particularly it relates to a method of treating a virus-infected host with a class of chemical compounds at extremely low dosages in the order of about 250 picograms ($10^{-12}$ grams; pg) to 250 micrograms ($10^{-6}$ grams; μg) per kilogram of host body weight. The difference between a picogram and a milligram is the same as the difference between one and one billion.

The compounds which are active in the practice of the present invention are those having a stereochemically unencumbered access to a nitrogen-nitrogen bond. The compounds within the purview of the invention are exemplified by those having the following formula:

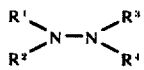

(1)

where $R^1$, $R^2$, $R^3$ and $R^4$ are selected from the class consisting of hydrogen, lower alkyl, aryl, heterocyclic aryl, $COR^5$, $CSR^5$, $CONHR^5$, $SO_2R^5$ where $R^5$ is lower alkyl, aryl, heterocyclic aryl, amino, lower alkoxy and adamantyl, with the proviso that $R^1$ and $R^2$ or $R^3$ and $R^4$ are different where $R^1$ or $R^3$ is $COR^5$, $CSR^5$, $CONHR^5$ or $SO_2R^5$. $R^1$ and $R^2$ or $R^3$ and $R^4$ or $R^1$ and $R^3$ when taken together may be selected from the class consisting of substituted alkylidene and substituted azo. $R^3$ and $R^4$ taken together may be substituted alkylidene. $R^2$ and $R^4$ may be a valence bond between the two nitrogens. As used herein the terms lower alkyl, lower alkoxy and the like define groups having 1 to about 6 carbons.

One of the problems in the field of virology has been the absence of predictability in chemoprophylaxis. Indeed, there had existed a belief among some authorities that chemoprophylaxis would not be successful in the treatment of virus infections. Up to the present time there has been no predictability with regard to the antiviral effect of particular compounds with the exception of certain compounds known to induce interferon. A compound may not be active while its homolog or a substituent is quite active. An indicated activity is frequently not reproducible with the same compound in the same dosage.

In the entire field of virology, only three compounds have been made commercially available that have antiviral effects in humans and all of these have been effective against a limited group of viruses. One of them is a compound for the treatment of kerotitis due to Herpes simplex virus. Another is a compound effective against particular strains of Influenza, and the third is a compound effective in the chemoprophylaxis of smallpox and some of the complications of vaccination.

The exact requirements for a successful antiviral compound have not been determined. Besides the chemical nature of the compound, other factors that may be involved are solubility, permeability, particle size and the like. It has been suggested that a successful antiviral agent may not attack a virus directly but rather may stimulate factors of host resistance. An effective chemoprophylactic compound is one which would have effect against a broad spectrum of virus-induced diseases, and would be effective in oral administration. Ideally, the chemoprophylactic nature of the compound should be identifiable with a particular portion of its chemical molecule and be modifiable by substituents added to the basic molecule portion. Also the therapeutic index should preferably be large, over about 100. The therapeutic index is the ratio of an acute toxic dose to an effective dose in a given host. No compund is known up to the present time which meets the ideal.

DISCUSSION

The compounds of the present invention were discovered in an antiviral screening program that was designed, among other things, to detect augmentation of host resistance. Hundreds of compounds were tested, and in the thousands of tests over this period, there was not another single instance in which a previously untested compound showed protection of more than 3 animals out of 10 at the survival level. With the compounds of the present invention from 3 to 6 survivors were observed.

Four reference compounds known to have antiviral activity have been used for comparative purposes. These are statolon, pyran copolymer, amantadine and methisazone. All of these compounds have been found to be below the ideal activity. Statolon, an interferon inducer, showed a high degree of protection against many viral infections of animals, but it is totally inactive on oral administration. Pyran copolymer, also an interferon inducer, was active only against Mengo virus infection, the most sensitive virus to interferon, and its activity was so weak that negative results were obtained with other viruses. Methisazone was active againt pox virus infections of mice, but its activity is limited specifically to pox viruses, and a large dose of compound is necessary. Amantadine and related compounds have been tested. In 18 tests of amantadine on Ann Arbor Influenza virus, the most sensitive virus to amantadine, survivors were seen only on five occasions. In the other 13 tests protection was either not evident or was only at the increased geometric mean survival time level. In 41 tests with Influenza virus PR 8, there was only one single instance of a statistically significant number of survivors (3), and 11 instances of increased geometric mean survival time indicated by the computer. Amantadine was inactive against all of the other viruses in the test system.

The most active of the compounds of this invention are active against all of the types of Influenza against which they have been tested. On a weight basis, the compounds of this invention are a great deal more active on Influenza than the amantadines. Intrinsically, comparing the maximum protective response to the optimal dose under optimal conditions the compounds of the present invention are far better than amantadine against Ann Arbor Influenza viruses. In only one single experiment out of about 30 experiments, amantadine had a larger number of survivors than the compounds of this invention. With other compounds reported to have chemoprophylactic activity, the dose range was greatly in excess of the dose ranges found effective in the present invention.

Without wishing to be bound by a theory of operation it is believed that because of the unusual nature of the activity of the compounds of this invention, their broad spectrum, and inactivity in tissue vulture, that the action of the compounds is on the host rather than on the host-virus relationship. It is believed that the activity is not the induction of interferon for it shows no activity in tissue culture as interferon does. They are weakly active on Mengo Virus infections of mice, the most sensitive strain to interferon, and no known interferon inducer is active orally, whereas the compounds of this invention are most effective when administered orally.

What is believed to be the most closely related prior art is described below. A literature search on antiviral activity of hydrazine, semicarbazide and thiosemicarbazide developed the following publications. No publication was found that reported activity of the compounds of the present invention at the very low dose levels that have not been found to be effective. There is no known prior art describing chemoprophylactic activity against a broad spectrum of viruses by orally administered compounds.

1. "In Vitro Antiviral Activity of Hydrazine Sulfate". B. Loddo, et al. *Experientia* 20: 326 (1964). In this paper it is reported that hydrazine sulfate is active in preventing polio and Vaccinia virus multiplication in vitro as determined by cytopathic effect in human amnion cells (Mascoli's line), and antiviral activity was reported at concentrations of from 8 to 66 micrograms per milliliter (μg/ml). This is an insensitive test influenced by numerous factors, pH, and the like, in which the growth of the virus is measured in culture medium in the presence of the compound.

In the present study of hydrazine sulfate, the more sensitive and satisfactory plaque reduction technique was used, and it was found that at the reported concentrations hydrazine was toxic to the cells. At concentrations of from 10 to 100 milligrams per milliliter (mg/ml), toxic effects on the cells were clearly evident on microscopic observation, and below the level of toxicity, no antiviral activity was demonstrated. It is well known in virology that cells injured due to toxic substances will not support the growth of viruses. It is believed that Loddo et al. reported the toxic effects of hydrazine sulfate on cells as being antiviral and that their claim of antiviral activity at the concentrations used is an erroneous interpretation of their data. It has been found that hydrazine was more toxic than most of its derivatives which exhibit no cytotoxicity at levels from 50 to 100 mg/ml.

2. "Inhibitory Activity of Benzoyl Hydrazides and Hydrazine on the Growth of Influenza Virus in Chick Embryo Lung Tissue Culture". W.D. Kundin, et al. *Experientia* 20: 438–9 (1964). The authors report on the activity of hydrazines and some derivatives in preventing the growth of Influenza virus on embryonic chick lung tissue. The toxicity of the compounds on the tissue cultures used was established and was found to range from 0.016 to 2 mg/ml. The maximum concentration of drug inhibitory to the virus was found to range from 0.002 to .25 mg/ml; therefore, the therapeutic index was 8. As mentioned in relation to the Loddo et al. reference above, cells under toxic influences do not grow viruses. In this paper the inhibitory effect reported as due to the compounds appears to be a misinterpretation of the experiment and may actually be due to the toxic activity of the compound on the cells.

3. "Potential Antiviral Thiourea Derivatives". Ng. Ph. Buu-Hoi, et al. *J. Chem. Soc.* 1956, 2160–5. In this paper the authors show that several compounds containing a nitrogen-nitrogen bond have antiviral activity and report on the chemical synthesis of several compounds containing this linkage. The details of the antiviral tests are not given in the above paper, but are reported in *Compt. rend.*, 1954, 238, 2583 (Buu-Hoi, et al.). All activity is reported at relatively high doses, and they did not test at the low dose levels found essential for a broad spectrum of activity.

4. There are many papers in the literature by Dr. John Bauer and his associates on the Effects of Methisazone on pox viruses. The activity of methisazone is altered greatly by very slight changes on the side chains of the semicarbazide. Relatively high doses are necessary for protective effects. There is no reported activity against any viruses other than pox viruses. There are no reports in the literature on the activity of methisazone or related compounds against either RNA or DNA viruses at low concentration.

5. In a paper by Cifuentas-Bernal et al. "Treatment of Infectious Canine Hepatitis with a Monoamine Oxidase Inhibiting Drug", Toxicology and Applied Pharmacology 12, 508–517 (1968), a study was made on the treatment of infectious canine hepatitis with a monoamine oxidase inhibiting drug, nialamide. The rationale was to determine if monamine oxidase inhibiting drugs that have been reported to protect against hepatic damage might reduce the hepatic injury in cases of infectious canine hepatitis and thus protect the animals. At doses of 50 milligrams per kilogram (mg/kg) of body weight, protection was found when 15 of 16 treated animals survived and 5 of 6 control animals died. In the paper no mention is made of treatment with very low doses. The authors describe the action of nialamide as the inhibition of monoamine oxidase.

6. Methylgloxal-bis-guanylhydrazone (methyl-GAG) is known to reduce haemagglutination (HA) titres of Influenza A PR8 virus multiplying in chorioallantoic membrane (CAM) cultures and in embryonated eggs. The treatment ranged from 0.125 to 1000 mg. methyl-GAG per ml. Ninety percent inhibition was obtained at the lower limit while the upper limit was toxic. C. Kuchler et al. Acta virol. 12:441–445, 1968.

OBJECTS OF THE INVENTION

It is an object of the present invention to provide antiviral dose forms which are effective in oral administration.

It is another object of this invention to provide chemical compounds which are effective against viral diseases which have predictable and reproducible behavior in known doses.

It is another object of the present invention to identify compounds having antiviral activity at a high therapeutic index.

It is a further object of the present invention to provide a method of antagonizing viral diseases by chemoprophylaxis.

It is another object of this invention to identify a class of compounds having a readily recognizable characteristic structure in which all members are chemoprophylactic compounds.

It is another object of the present invention to provide a method of treating viral infections in lower animals, such as laboratory experimental animals, household pets, farm animals, and show or exhibition animals, including white mice and the like.

It is another object of the present invention to provide a method of recognizing and selecting compounds which are of practical application in veterinary medicine.

SUMMARY OF THE INVENTION

It has been found that certain compounds exert a pronounced chemoprophylactic effect on viral infections of animals. The compounds found effective to date in the practice of this invention are hydrazine, hydrazine sulfate; semicarbazide, hydrochloride, thiosemicarbazide; 2-butanone, thiosemicarbazone; aminoguanidine, bicarbonate, isoniazid; hydralazine; methisazone; [(2,6-dichlorobenzylidine)amino]guanidine acetate; 3-pentanone, thiosemicarbazone; 2-pentanone, thiosemicarbazone; acetone, thiosemicarbazone; 1-(sec-butylideneamino)guanidine, nitrate; acetoacetic acid, ethyl ester, thiosemicarbazone; 1,2-dimethylhydrazine, dihydrochloride; 1,1-dimethylhydrazine; methylhydrazine; 2-indanone, thiosemicarbazone; cyclopentanone, 3-thio-4-o-tolylsemicarbazone.

It has been found that compounds which afford unencumbered access to a nitrogen-nitrogen bond are active. The compounds are active against both ribonucleic acid (RNA) type viruses and desoxyribonucleic acid (DNA) type viruses. All of the above named compounds have been shown to be active on at least one viral infection, and as a class of compounds they have been shown to be effective in protecting mice against Herpes and vaccinia viruses (DNA viruses), as well as strains A, $A_1$ and B of Influenza virus, and Mengo and Columbia SK Polio viruses (RNA viruses). Chemoprophylaxis has been demonstrated in three animal species. Chick embryos have been protected against Herpes virus; the course of Vaccinia infection of the rabbit skin has been modified, and protection is afforded against all of the above-named viruses in the mouse. The compounds show no activity in tissue culture. They have the unique property of protecting animals at remarkably low concentrations and surprisingly are inactive at higher doses. Under optimum conditions the preferred dose appears to lie between 250 nanograms ($10^{-9}$ grams; ng) and 250 micrograms per kilogram, but activity has been demonstrated with total doses as low as 250 picograms (pg) per kilogram of host body weight. The acute toxicity of the more toxic compounds is about 25 milligrams per kilograms per kilogram, and therefore the effective dose is less than one-one-thousandth of the acute toxic dose.

Optimal efficacy is dependent upon a dose-dose schedule relationship, appearing to be more active when a dose is administered at 48 hour intervals, with prolonged pre-treatment. Administration of the drugs at 48 hour intervals for up to 6 days prior to virus challenge appears to increase the overall efficacy of the procedure, increasing the percentage of the animals that survive the virus challenge. In such a method of treatment activity is demonstrated over a wide range of doses, several ten-fold dilutions.

All of the compounds tested are as effective, or more effective on oral administration as they are on parenteral administration. Often, under optimal conditions of adminstration, from 30 to 60 percent (%) of the treated animals survive the virus challenge—an overwhelming lethal infection in which 100% of the control animals are almost invariably killed. There is no dose response curve in the usual sense. A protective effect is observed which is more pronounced with the proper dose-dose schedule relationship.

DETAILED DESCRIPTION

It has been found that the compounds of the present invention are active prophylactically against many viral diseases of animals. It has been found that, of the DNA viruses, mice are protected against Herpes simplex virus. The activity of the compounds of the present invention on Herpes also can be demonstrated in eggs where a protective effect upon the intact embryo is exerted. Vaccinia infections of the mouse tail have been shown to be modified by the compounds of the present invention as is Vaccinia infection of the rabbit skin. Neurovaccinia in the mouse brain (an overwhelming infection) has been shown statistically to be influenced. Among the RNA viruses, Influenza A (PR 8), Influenza $A_1$ (Ann Arbor), Influenza B (Mass.) and Influenza B (Maryland) are influenced by the compounds of the present invention. Mengo virus infection in mice is moderately sensitive to the compounds that have been tested. Activity has been found against Columbia SK polio in mice.

In a preliminary study, the protective effect of the compounds of this invention was evident using statistical techniques and rarely was there protection at the survival level. As methodology was perfected it was found that the best results were obtained on oral administration of the drugs and when they were administered at 48 hour intervals with one to three or more doses prior to infection. With these conditions three, four, or even five survivors of 10 animals in a group are found. This degree of protection is highly significant because these are overwhelming infections in which 100% of the controls almost invariably die. However, highly lethal infections must be used to provide laboratory guides for the treatment of diseases of higher animals which are quite mold by comparison, particularly upper respiratory diseases, where only a minute fraction of the total cells of the body are involved.

It also has become evident that the protective effect of the compounds of this invention is most dramatic when the virus challenge is low and, as mentioned above, in many of the diseases of higher animals for which prophylactic approaches are feasible, the virus challenge also is very low. Better results are obtained where the virus challenge is equal to the challenge that kills 50 percent of the hosts ($LD_{50}$) than where the challenge is three times $LD_{50}$.

It has long been recognized that to be widely used, a chemoprophylactic antiviral agent should have certain properties. It should be active on oral administration. It should be active at a minute fraction of its toxic dose and have no unfavorable side effects. It should protect against a wide range of different and unrelated viral agents, and it should be effective when administered over a long period of time, with no development of insensitivity to the substance or resistance in the virus.

Not all compounds with a nitrogen-nitrogen bond have equal activity, and there may be a difference in susceptibility of different viruses to different compounds.

Tests of thiosemicarbazone on Vaccinia in the rabbit skin have been reasonably consistent with highly significant diminution of pox formation at narrow dose levels, 0.25 or 2.5 micrograms per kilogram of host body weight ($\mu g/kg$). Results with 2-butanone, thiosemicarbazone have been variable, and the reasons for this have not yet been determined.

In order more clearly to disclose the nature of the present invention, specific examples of the practice of the invention are hereinafter given. It should be understood, however, that this is done solely by way of example and is intended neither to delineate the scope of the invention nor limit the ambit of the appended claims.

In the tables the virus used in the test is indicated at the top together with the host, the dose schedule and the route of administration. In each test, not otherwise described, there were 10 animals at each dose level, and 20 controls. The tables are summaries of the observations showing, for each dose level, the number of animals surviving at the end of the experiment, the number surviving for 1 day or longer after 100% of the controls were dead, and the number of animals surviving after approximately 80 to 90% of the controls were dead. As 20 control animals were used and 10 test animals, in order to make a direct comparison, the number of surviving control animals has been divided by two, thus if three control animals survive at 8 days it would be recorded as 1½ animals. To control the influence of stress, each time a treated group was administered a dose of drug, the control animals were administered a dose of saline or distilled water by the same route.

As used herein, the abbreviation "NS" means "not significant". The symbol "-" before a number in a dose schedule indicates the number of hours prior to infection that the dose was administered. The symbol "+" before a number in a dose schedule indicates the number of hours after infection that the dose was administered.

EXAMPLE 1

The following example illustrates the effect of test compounds against Herpes virus in mice. The results are shown in tables 1-9 and 50.

It was found that Herpes virus was quite sensitive to the action of the compounds of this invention and the Herpes virus test was used to determine those compounds that had antiviral activity. As the work progressed it became increasingly clear that small doses gave the best results, and later it was found that drug administered at 48 hour intervals gave even better results.

Early in the studies it was found that more consistent and uniform results could be obtained when the drum was given orally rather than parenterally, and for this reason almost all of the experiments were conducted using oral administration.

In the earlier stages significance was at the increased geometric mean survival time level, and it was rare that there was statistical significance at the survival level. As more optimal conditions were found it was not uncommon, although not uniform, to find 3, 4 or 5 of the treated animals surviving. (Tables 1,2,3,4). Earlier in this work it was found that the antiviral activity consisted of protecting an occasional animal so that it survived throughout the experiment, resulting in the computer recording the observation as statistically significant at the geometric mean survival time level, and in these instances usually the remaining treated animals died at almost exactly the same rate as the controls. (Table 50). When more optimal conditions were determined and used many of the treated animals survived after most of the control animals died. (Table 5).

When it was found that surprisingly low doses of drug were most active and when these were used at 48 hour intervals, activity at significant levels was observed over a wide range of dose levels up to several log dilutions. Under non-optimal conditions more variable results were observed and activity often was found at a single dose level. (Table 4). This is typical of many experiments done under less than ideal conditions.

TABLE 1

Virus: Herpes Virus
Dose Schedule: −50, −25 pre-infection; +17, +65, +114 post-infection
Route of Administration: Oral
Host: Mouse

| Compound | | Total Dose Administered to the Animal in Micrograms | | | | | |
|---|---|---|---|---|---|---|---|
| | | 5 | .5 | .05 | .005 | .0005 | Control |
| Thiosemi-carbazide | Survivors | 1 | 3 | 3 | 4 | 3 | 0 |
| | No. animals surviving when 100% of controls are dead | 2 | 3 | 3 | 5 | 3 | 0 |
| | No. animals surviving after 7 days | 4 | 4 | 2 | 6 | 6 | 2½ |
| semicarba-zide | Survivors | 1 | 0 | 1 | 5 | 1 | 0 |
| | No. animals surviving when 100% of controls are dead | 2 | 1 | 2 | 5 | 1 | 0 |
| | No. animals surviving after 7 days | 7 | 4 | 5 | 8 | 5 | 2½ |
| hydrazine | Survivors | 2 | 1 | 0 | 4 | 3 | 0 |
| | No. animals surviving when 100% of controls are dead | 0 | 1 | 1 | 0 | 0 | 0 |
| | No. animals surviving after 7 days | 7 | 6 | 5 | 6 | 5 | 2½ |

TABLE 2

Virus: Herpes Virus
Dose Schedule: −50, −25 pre-infection; +17, +65, +114 post-infection
Route of Administration: Oral
Host: Mouse

| Compound | | Total Dose Administered to the Animal in Micrograms | | | | | |
|---|---|---|---|---|---|---|---|
| | | 5 | .5 | .05 | .005 | .0005 | Control |
| Thiosemi-carbazide | Survivors | 1 | 3 | 3 | 4 | 3 | 0 |
| | No. animals surviving when 100% controls are dead | 1 | 3 | 3 | 5 | 3 | 0 |
| | No. animals surviving after 9 days | 2 | 3 | 4 | 5 | 5 | ½ |
| semicar-bazide, hydro-chloride | Survivors | 1 | 0 | 1 | 5 | 1 | 0 |
| | No. animals surviving when 100% controls are dead | 2 | 1 | 2 | 0 | 0 | 0 |
| | No. animals surviving after 9 days | 4 | 1 | 3 | 7 | 4 | ½ |

TABLE 3

Virus: Herpes Virus
Dose Schedule: −96, −48 pre-infection; +1, +49, +97 post-infection.
Route of Administration: Oral.
Host: Mouse

| Compound | | Total Dose Administered to the Animal in Micrograms | | | | | |
|---|---|---|---|---|---|---|---|
| | | 5 | .5 | .05 | .005 | .0005 | Control |
| Thiosemi-carbazide | Survivors | 0 | 1 | 1 | 2 | 0 | ½ |
| | No. animals surviving when 19/20 controls are dead | 0 | 1 | 1 | 2 | 2 | ½ |
| | No. animals surviving after 8 days | 0 | 3 | 4 | 3 | 1 | 1 |
| semicarba-zide, hydro-chloride | Survivors | 3 | 5 | 4 | 2 | 1 | ½ |
| | No. animals surviving when 19/20 controls are dead | 4 | 5 | 4 | 2 | 1 | ½ |
| | No. animals surviving after 8 days | 5 | 5 | 4 | 3 | 1 | 1 |

TABLE 4

Virus: Herpes Virus
Dose Schedule: −48, −25 pre-infection; ±17, +65, +114 post-infection.
Route of Administration: Oral.
Host: Mouse

| Compound | | Total Dose Administered to the Animal in Micrograms | | | | | |
|---|---|---|---|---|---|---|---|
| | | .05 | .005 | .0005 | .00005 | .000005 | Control |
| Thiosemi-carbazide | Survivors | 0 | 0 | 0 | 3 | 0 | 1½ |
| | No. animals surviving when 17/20 controls are dead | 0 | 2 | 0 | 3 | 0 | 1½ |
| | No. animals surviving after 9 days | 1 | 5 | 2 | 6 | 2 | 3 |
| Isoniazid | Survivors | 1 | 1 | 0 | 2 | 3 | 1½ |
| | No. animals surviving when 17/20 controls are dead | 1 | 2 | 0 | 3 | 3 | 1½ |
| | No. animals surviving after 9 days | 2 | 3 | 4 | 5 | 3 | 3 |
| 2-Butanone, thiosemi-carbazone | Survivors | 0 | 2 | 4 | 3 | 0 | 1½ |
| | No. animals surviving when 17/20 controls are dead | 0 | 3 | 5 | 4 | 0 | 1½ |
| | No. animals surviving after 9 days | 3 | 4 | 6 | 8 | 1 | 3 |

TABLE 5

Virus: Herpes Virus
Dose Schedule: −52, −22 pre-infection; +19, +65, +114 post-infection.
Route of Administration: Oral.
Host: Mouse

| Compound | | Total Dose Administered to the Animal in Micrograms | | | | | | |
|---|---|---|---|---|---|---|---|---|
| | | .05 | .005 | .0005 | .00005 | .000005 | .0000005 | Control |
| Hydralazine | Survivors | 0 | 2 | 2 | 0 | 0 | 1 | 0 |
| | No. Animals surviving when 100% controls are dead | 0 | 2 | 2 | 0 | 0 | 1 | 0 |
| | No. animals surviving after 8 days | 1 | 3 | 2 | 2 | 4 | 1 | 1 |
| Methisa-zone | Survivors | 0 | 0 | 1 | 3 | 1 | 1 | 0 |
| | No. animals surviving when 100% controls are dead | 0 | 0 | 1 | 4 | 1 | 1 | 0 |
| | No. animals surviving after 8 days | 2 | 3 | 3 | 4 | 3 | 4 | 1 |

TABLE 6

Virus: Herpes Virus
Dose Schedule: −48 pre-infection; +4, +52, +96, +120 post-infection.
Route of Administration: Oral.
Host: Mouse

| Compound | | Total Dose Administered to the Animal in Micrograms | | | | |
|---|---|---|---|---|---|---|
| | | .005 | .0005 | .00005 | .000005 | Control |
| semicar-bazide | Survivors | 0 | 1 | 1 | 0 | 0 |
| | No. animals surviving when 100% of controls are dead | 0 | 1 | 2 | 1 | 0 |
| | No. animals surviving after 9 days | 1 | 1 | 3 | 1 | 1½ |

TABLE 7

Virus: Herpes Virus
Dose Schedule: −120, −72, −24 pre-infection; +24, +72 post-infection
Route of Administration: Oral
Host: Mouse

| Compound | | Total Dose Administered to the Animal in Micrograms | | | | |
|---|---|---|---|---|---|---|
| | | .005 | .0005 | .00005 | .000005 | Control |
| Isoniazid | Survivors | 0 | 1 | 0 | 0 | 0 |
| | No. animals surviving when 100% of controls are dead | 1 | 1 | 0 | 0 | 0 |
| | No. animals surviving after 6 days | 2 | 3 | 0 | 1 | 1 |
| Hydrala-zine | Survivors | 0 | 0 | 1 | 0 | 0 |
| | No. animals surviving after 100% of controls are dead | 0 | 1 | 1 | 0 | 0 |
| | No. animals surviving after 6 days | 1 | 1 | 2 | 0 | 1 |
| Methisa-zone | Survivors | 1 | 0 | 0 | 0 | 0 |
| | No. animals surviving when 100% of controls are dead | 0 | 0 | 0 | 0 | 0 |
| | No. animals surviving after 6 days | 0 | 0 | 0 | 1 | 1 |

TABLE 8

Virus: Herpes Virus
Dose Schedule: −96, −48 pre-infection; +1, +49, +97 post-infection.
Route of Administration: Oral
Host: Mouse

| Compound | | Total Dose Administered to the Animal in Micrograms | | | | | |
|---|---|---|---|---|---|---|---|
| | | 5 | .5 | .05 | .005 | .0005 | Control |
| hydrazine | Survivors | 2 | 0 | 2 | 3 | 3 | ½ |
| | No. animals surviving when 19/20 of controls are dead | 2 | 1 | 2 | 3 | 5 | ½ |
| | No. animals surviving after 8 days | 2 | 1 | 3 | 6 | 6 | 1 |

TABLE 9

Virus: Herpes Virus
Dose Schedule: −120, −75, −24 pre-infection; ±24, +72 post-infection
Route of Administration: Oral.
Host: Mouse

| Compound | | Total Dose Administered to the Animal in Micrograms | | | | | | |
|---|---|---|---|---|---|---|---|---|
| | | .05 | .005 | .0005 | .00005 | .000005 | .0000005 | Control |
| Isoniazid | Survivors | 1 | 1 | 0 | 1 | 2 | 1 | 0 |
| | No. animals surviving when 100% controls are dead | 1 | 1 | 0 | 1 | 2 | 1 | 0 |
| | No. animals surviving after 8 days | 4 | 1 | 1 | 1 | 2 | 4 | 3½ |
| Hydralazine | Survivors | 2 | 1 | 1 | 1 | 1 | 1 | 0 |
| | No. animals surviving when 100% controls are dead | 2 | 1 | 2 | 3 | 1 | 1 | 0 |
| | No. animals surviving after 8 days | 3 | 2 | 3 | 4 | 2 | 1 | 3½ |
| Methisa-zone | Survivors | 0 | 1 | 0 | 2 | 1 | 0 | 0 |
| | No. animals surviving when 100% controls are dead | 0 | 1 | 0 | 3 | 1 | 0 | 0 |
| | No. animals surviving after 8 days | 1 | 3 | 1 | 4 | 3 | 3 | 3½ |

EXAMPLE 2

The following example illustrates the effect of test compounds of this invention against Herpes virus in eggs. The results are shown in Table 10.

Chicken eggs were injected with a single dose of several hydrazine drugs administered in the allantoic cavity 24 hours prior to infection with Herpes virus in yolk sac. (Table 10). All of the 24 controls were dead at the end of the 4th day, and a small percentage of the embryos survived longer than the controls, a few being alive at the 22nd day. Nine of those that were alive were helped to hatch and live baby chicks were walking around the incubator. It was impressive to see living chicks surviving on the 22nd day a virus challenge that killed all of the controls on the 4th day. This is unequivocal evidence that the compounds are active on Herpes virus in eggs.

TABLE 10

Herpes Virus in Eggs.

Virus: Herpes
Dose Schedule: Single Dose 24 hours pre-infection.
12 eggs used in each test, each egg weighing 50 to 60 grams.
All controls died on the 4th day.

| Compound | Total Dose in μg | Deaths on Days | | | | Total Deaths-4th Day | No. Dying 5-22 Day | No. Living Longer Than Controls | No. Hatched |
|---|---|---|---|---|---|---|---|---|---|
| | | 1 | 2 | 3 | 4 | | | | |
| Control | 0 | | 4 | 8 | 10 | 2 | 24/24 | | |
| Semicar-bazide | .00005 | 4 | 3 | 4 | | 11 | 1 | 1 | |
| | .0005 | 2 | 2 | 6 | 1 | 11 | 0 | 1 | 1 |
| | .005 | 2 | 2 | 3 | | 7 | 2 | 4 | 1 |
| | .05 | 1 | 4 | 6 | | 11 | 0 | 1 | |
| | .5 | 2 | 2 | 5 | | 9 | 2 | 2 | |
| | 2 | 2 | 2 | 3 | 3 | 10 | 0 | 0 | |
| | 20 | 3 | 1 | 5 | 2 | 11 | 0 | 1 | |
| Total | | | | | | | | 10 | 2 |

TABLE 10-continued

Herpes Virus in Eggs
Virus: Herpes
Dose Schedule: Single Dose 24 hours pre-infection.
12 eggs used in each test, each egg weighing 50 to 60 grams.
All controls died on the 4th day.

| Compound | Total Dose in μg | Deaths on Days 1 | 2 | 3 | 4 | Total Deaths-4th Day | No. Dying 5–22 Day | No. Living Longer Than Controls | No. Hatched |
|---|---|---|---|---|---|---|---|---|---|
| Control | 0 | 4 | 8 | 10 | 2 | 24/24 | | | |
| 2-Butanone thiosemi-carbazone | .00005 | 2 | 4 | 5 | | 11 | 0 | 1 | 1 |
| | .0005 | 1 | 5 | 3 | 1 | 10 | 0 | 2 | 1 |
| | .005 | 2 | 4 | 2 | 3 | 11 | 0 | 1 | |
| | .05 | 2 | 6 | 3 | | 11 | 1 | 1 | |
| | .5 | 1 | 3 | 6 | 2 | 12 | 0 | 0 | |
| | 2 | 1 | 5 | 3 | | 9 | 2 | 3 | 1 |
| | 20 | | 5 | 1 | 2 | 8 | 1 | 4 | 2 |
| Total | | | | | | | | 12 | 5 |
| Thiosemi-carbazide | .00005 | 2 | 5 | 2 | 1 | 10 | 0 | 1 | |
| | .0005 | 2 | 3 | 2 | 3 | 10 | 0 | 1 | not |
| | .005 | 4 | 3 | 3 | | 10 | 1 | 2 | helped |
| | .05 | | 3 | 5 | | 9 | 0 | 1 | to |
| | .5 | 3 | 4 | 2 | 2 | 11 | 0 | 1 | hatch |
| | 2 | 3 | 1 | 5 | 3 | 12 | 0 | 0 | |
| | 20 | 1 | 4 | 6 | 1 | 12 | 0 | 0 | |
| Total | | | | | | | | 7 | |
| Hydrazine | .00005 | 2 | 2 | 5 | | 9 | 0 | 1 | |
| | .0005 | 2 | 6 | 4 | | 12 | 0 | 0 | |
| | .005 | | 7 | 4 | | 11 | 0 | 0 | |
| | .05 | 2 | 5 | 3 | | 10 | 0 | 0 | |
| | .5 | 2 | 2 | 5 | 1 | 10 | 0 | 0 | |
| | 2 | 3 | 4 | 1 | 1 | 9 | 0 | 1 | 1 |
| | 20 | 3 | 2 | 4 | 2 | 11 | 0 | 1 | 1 |
| Total | | | | | | | | 3 | 2 |

EXAMPLE 3

The following example illustrates the effect of the test compounds against Influenza Ann Arbor virus. The results are shown in Tables 11–30. The effect of the hydrazine compounds on the Ann Arbor strain of Influenza virus was studied in mice. It is evident with this virus that optimal results were obtained on oral administration. As illustrated in Table 11, when semicarbazide was administered subcutaneously there was a total of only three survivors at four dose levels, whereas under oral administration under similar conditions, there were ten survivors. Tables 12 and 13 present interesting results because they show quite clearly the upper and lower limits of activity, there being no activity at 500 μg and none at 0.05 μg or below, with significant survivors in the three dose levels in between. Under more optimal conditions of administration it appears that a larger dose of drug is needed to give maximum protective effect. This protective effect is demonstrable over several log dilutions of drug, whereas without optimal conditions activity was only demonstrable over a narrow dose range. The data suggest that with different compounds different dilutions of drug may yield optimal results. Table 14 shows that aminoguanidine at 30 μg, the maximum dose level used, is the most active. This indicates that with some of the other compounds of this invention a larger dose may be necessary to give the most effective results.

At times there are unexplained and apparently uncontrolled variations between very similar experiments. A comparison of Tables 12, 13 and 15 may illustrate this. Hydrazine was tested in two experiments on different dates but using identical procedures and techniques. There are slight differences between the two that illustrate one type of uncontrolled variation that is encountered. The same virus suspension was used on different dates in these experiments. If Table 15 is compared with these, the only difference being that here the oral route of administration was used, it is evident that much less significant activity was demonstrated. This experiment was done with a new lot of virus and the control animals died much more quickly—there being a more severe virus challenge. Similar observations have been made with Influenza Virus, PR 8, in which with several virus challenges few survivors are evident. This may indicate that the protective effect of the compounds of this invention is most pronounced when the virus challenge is not overwhelming. The observations on Vaccinia in the mouse tail and Vaccinia in the rabbit skin both support this concept.

TABLE 11

Virus: Influenza, Ann Arbor
Dose Schedule: −24 pre-infection; +24, +72, +96 post-infection
Route of Administration: Subcutaneous and oral
Host: Mouse

| Compound | Total Dose Administered to the Animal in Micrograms | | | | |
|---|---|---|---|---|---|
| | .5 | .05 | .005 | .0005 | Control |
| Route of Administration: Subcutaneous | | | | | |
| semicarbazide Survivors | 1 | 0 | 1 | 1 | 0 |
| No. animals surviving when 100% of controls | | | | | |

TABLE 11-continued

Virus: Influenza, Ann Arbor
Dose Schedule: −24 pre-infection; +24, +72, +96 post-infection
Route of Administration: Subcutaneous and oral
Host: Mouse

| Compound | | Total Dose Administered to the Animal in Micrograms. | | | | |
|---|---|---|---|---|---|---|
| | | .5 | .05 | .005 | .0005 | Control |
| | are dead | 1 | 0 | 1 | 2 | 0 |
| | No. animals surviving after 9 days | 1 | 0 | 2 | 4 | 1½ |
| Route of Administration: Oral. | | | | | | |
| semicarb-azide | Survivors | 3 | 3 | 1 | 3 | 0 |
| | No. animals surviving when 100% of controls are dead | 3 | 3 | 1 | 3 | 0 |
| | No. animals surviving after 9 days | 3 | 3 | 1 | 3 | 1½ |

TABLE 12

Virus: Influenza, Ann Arbor, Virus
Dose Schedule: −24 pre-infection, +24, +72 post-infection
Route of Administration: Subcutaneous.
Host: Mouse

| Compound | | Total Dose Administered to the Animal in Micrograms | | | | | | | | |
|---|---|---|---|---|---|---|---|---|---|---|
| | | 500 | 50 | 5 | .5 | .05 | .005 | .0005 | .00005 | Control |
| hydrazine, hydrate | Survivors | 0 | 1 | 3 | 3 | 0 | 0 | 0 | 0 | 0 |
| | No. animals surviving when 100% controls are dead | 0 | 3 | 3 | 3 | 0 | 1 | 2 | 0 | 0 |
| | No. animals surviving after 7 days | 6 | 7 | 6 | 7 | 4 | 3 | 5 | 1 | 1½ |

TABLE 13

Virus: Influenza, Ann Arbor, Virus
Dose Schedule: −24 pre-infection; +24, +72 post-infection.
Route of Administration: Subcutaneous.
Host: Mouse

| Compound | | Total Dose Administered to the Animal in Micrograms | | | | | | | | |
|---|---|---|---|---|---|---|---|---|---|---|
| | | 500 | 50 | 5 | .5 | .05 | .005 | .0005 | .00005 | Control |
| hydrazine, hydrate | Survivors | 0 | 0 | 2 | 0 | 1 | 2 | 2 | 0 | 0 |
| | No. animals surviving when 100% controls are dead | 2 | 2 | 5 | 1 | 3 | 2 | 5 | 0 | 0 |
| | No. animals surviving after 5 days | 3 | 4 | 6 | 5 | 6 | 4 | 7 | 1 | 4 |

TABLE 14

Virus: Influenza, Ann Arbor, Virus
Dose Schedule: −24 pre-infection; +24, +72 post-infection
Route of Administration: Oral and subcutaneous
Host: Mouse

| Compound | | Total Dose Administered to the Animal in Micrograms | | | | | | |
|---|---|---|---|---|---|---|---|---|
| | | 30 | 3 | .3 | .03 | .003 | .0003 | Control |
| Route of Administration: Oral | | | | | | | | |
| amino-guanidine | Survivors | 5 | 3 | 4 | 2 | 1 | 1 | 0 |
| | No. animals surviving when 100% of controls are dead | 6 | 5 | 4 | 3 | 1 | 1 | 0 |
| | No. animals surviving after 7 days | 8 | 8 | 7 | 7 | 7 | 6 | 3½ |
| Route of Administration: Subcutaneous. | | | | | | | | |
| amino- | Survivors | 2 | 2 | 1 | 1 | 0 | 5 | 0 |

TABLE 14-continued

Virus: Influenza, Ann Arbor, Virus
Dose Schedule: −24 pre-infection; +24, +72 post-infection
Route of Administration: Oral and subcutaneous
Host: Mouse

| Compound | | Total Dose Administered to the Animal in Micrograms | | | | | | |
|---|---|---|---|---|---|---|---|---|
| | | 30 | 3 | .3 | .03 | .003 | .0003 | Control |
| quanidine | No. animals surviving when 100% of controls are dead | | 2 | 2 | 2 | 3 | 6 | 0 |
| | No. animals surviving after 7 days | | 6 | 7 | 7 | 8 | 8 | 3½ |

TABLE 15

Virus Influenza, Ann Arbor
Dose Schedule: −24 pre-infection; +24, +72 post-infection.
Route of Administration: Oral.
Host: Mouse

| Compound | | Total Dose Administered to the Animal in Micrograms | | | | | | | | |
|---|---|---|---|---|---|---|---|---|---|---|
| | | 500 | 50 | 5 | .5 | .05 | .005 | .0005 | .00005 | Control |
| Methisazone | Survivors | 0 | 0 | 0 | 0 | 0 | 0 | 0 | 0 | |
| | No. animals surviving when 100% controls are dead | | 1 | 2 | 2 | 0 | 0 | 3 | 1 | 0 |
| | No. animals surviving after 5 days | | 3 | 4 | 6 | 4 | 5 | 5 | 6 | 2½ |
| hydrazine hydrate | Survivors | 0 | 0 | 0 | 0 | 1 | 0 | 0 | 0 | 0 |
| | No. animals surviving when 100% controls are dead | 3 | 1 | 2 | 2 | 2 | 1 | 4 | 4 | 0 |
| | No. animals surviving after 5 days | 5 | 4 | 4 | 6 | 3 | 3 | 6 | 6 | 2½ |

TABLE 16

Virus: Influenza, Ann Arbor
Dose Schedule: −120, −72, −24 pre-infection; +24, +72, +120 post-infection.
Route of Administration: Oral.
Host: Mouse

| Compound | | Total Dose Administered to the Animal in Micrograms | | | |
|---|---|---|---|---|---|
| | | .5 | .05 | .005 | Control |
| semicarbazide | Survivors | 0 | 0 | 0 | 0 |
| | No. animals surviving when 100% of controls are dead | 0 | 0 | 0 | 0 |
| | No. animals surviving after 8 days | 0 | 0 | 1 | 2½ |
| Thiosemicarbazide | Survivors | 0 | 1 | 1 | 0 |
| | No. animals surviving when 100% of controls are dead | 3 | 1 | 1 | 0 |
| | No. animals surviving after 8 days | 3 | 4 | 1 | 2½ |
| Isoniazid | Survivors | 1 | 1 | 2 | 0 |
| | No. animals surviving when 100% of controls are dead | 1 | 1 | 2 | 0 |
| | No. animals surviving after 8 days | 1 | 2 | 2 | 2½ |

TABLE 17

Virus: Influenza, Ann Arbor
Dose Schedule:
−140, −96, −48 pre-infection; 0, +48, +96 post-infection.
Route of Administration: Oral.
Host: Mouse

| Compound | | Total Dose Administered to the Animal in Micrograms. | | | |
|---|---|---|---|---|---|
| | | .5 | .05 | .005 | Control |
| semi- carba- zide | Survivors | 1 | 1 | 1 | 0 |
| | No. animals surviving when 100% of controls are dead | 1 | 1 | 1 | 0 |
| | No. animals surviving after 8 days | 3 | 2 | 4 | 2½ |
| thio- semi- carba- zide | Survivors | 0 | 2 | 1 | 0 |
| | No. animals surviving when 100% of controls are dead | 2 | 3 | 1 | 0 |
| | No. animals surviving after 8 days | 6 | 5 | 2 | 3½ |
| Iso- nia- zid | Survivors | 2 | 2 | 2 | 0 |
| | No. animals surviving when 100% of controls are dead | 2 | 2 | 2 | 0 |
| | No. animals surviving after 8 days | 6 | 5 | 5 | 2½ |

TABLE 18

VIRUS: Influenza, Ann Arbor
Dose Schedule: −24 pre-infection; +24, +72 post-infection.
Route of Administration: Oral
Host: Mouse

| Compound [(2,6-dichlor- obenzylidine)- amino]guani- dine acetate | Total Dose Administered to the Animal | | | | | | | | | |
|---|---|---|---|---|---|---|---|---|---|---|
| | 3 mg | 300 µg | 30 µg | 3 µg | 300 ng | 30 ng | 3 ng | 300 pg | 30 pg | Control |
| Survivors | * | 0 | 0 | 0 | 0 | 0 | 0 | 1 | 0 | 0 |
| No. animals surviving when, 100% of controls are dead | * | 0 | 2 | 1 | 0 | 0 | 3 | 1 | 2 | 0 |
| No. animals surviving after 6 days | * | 1 | 3 | 2 | 1 | 1 | 4 | 2 | 4 | 2 |

* Toxic

TABLE 19

VIRUS: Influenza, Ann Arbor
Dose Schedule: −24; +24, +72
Route of Administration: Oral
Host: Mouse

| Compound 3-pentanone, thiosemi- carbazone | Total Dose Administered to the Animal | | | | | | | |
|---|---|---|---|---|---|---|---|---|
| | 150 µg | 120 µg | 90 µg | 60 µg | 24 µg | 18 µg | 12 µg | Control |
| Survivors | 1 | 1 | 0 | 0 | 0 | 1 | 0 | 0 |
| No. animals surviving when, 100% of controls are dead | 1 | 1 | 3 | 0 | 0 | 1 | 0 | 0 |
| No. animals surviving after 7 days | 2 | 1 | 3 | 1 | 0 | 1 | 1 | ½ |

TABLE 20

VIRUS: Influenza, Ann Arbor
Host: Mouse
Dose Schedule: −24 pre-infection; +24, +72 post-infection.
Route of Administration: Oral.

| Compound 3-pentanone, thiosemi- carbazone | Total Dose Administered to the Animal | | | | | | | | |
|---|---|---|---|---|---|---|---|---|---|
| | 300 µg | 30 µg | 3 µg | 300 ng | 30 ng | 3 ng | 300 pg | 30 pg | Control |
| Survivors | 0 | 0 | 1 | 0 | 0 | 0 | 0 | 0 | 0 |
| No. animals surviving when 100% of animals are dead | 3 | 3 | 3 | 1 | 0 | 0 | 1 | 0 | 0 |
| No. animals surviving after 6 days | 4 | 7 | 6 | 3 | 0 | 3 | 1 | 2 | 1 |

TABLE 21

VIRUS: Influenza, Ann Arbor
Host: Mouse
Dose Schedule: −24; +24, +72
Route of Administration: Oral.

| Compound 2-pentanone, thiosemicar- bazone | Total Dose Administered to the Animal | | | | | | | | |
|---|---|---|---|---|---|---|---|---|---|
| | 2.25 µg | 1.5 µg | 750 ng | 225 ng | 150 ng | 75 ng | 22.5 ng | 15 ng | Control |
| Survivors | 1 | 0 | 0 | 0 | 0 | 0 | 0 | 0 | 0 |
| No. animals surviving when, 100% of controls are dead | 1 | 0 | 1 | 1 | 0 | 0 | 0 | 1 | 0 |
| No. animals surviving after 7 days | 1 | 2 | 2 | 3 | 0 | 1 | 0 | 3 | ½ |

TABLE 22

VIRUS: Influenza, Ann Arbor
Host: Mouse
Dose Schedule: −24 pre-infection; +24, +72 post-infection.
Route of Administration: Oral.

| Compound 2-pentanone, thiosemi- carbazone | Total Dose Administered to the Animal | | | | | | | | |
|---|---|---|---|---|---|---|---|---|---|
| | 300 µg | 30 µg | 3 µg | 300 ng | 30 ng | 3 ng | 300 pg | 30 pg | Control |
| Survivors | 0 | 1 | 0 | 0 | 0 | 0 | 0 | 0 | 0 |
| No. animals surviving when, 100% of controls are dead | 0 | 1 | 1 | 1 | 1 | 1 | 0 | 2 | 0 |
| No. animals surviving after 6 days | 0 | 1 | 1 | 1 | 2 | 2 | 2 | 2 | 1 |

TABLE 23

VIRUS: Influenza, Ann Arbor
Host: Mouse
Dose Schedule: −24 pre-infection; +24, +72 post-infection.
Route of Administration: Oral.

| Compound acetone, thiosemi- carbazone | Total Dose Administered to the Animal | | | | | | | | |
|---|---|---|---|---|---|---|---|---|---|
| | 300 µg | 30 µg | 3 µg | 300 ng | 30 ng | 3 ng | 300 pg | 30 pg | Control |
| Survivors | 0 | 0 | 0 | 0 | 0 | 0 | 0 | 1 | 0 |
| No. animals surviving when, 100% of controls are dead | 0 | 1 | 4 | 0 | 2 | 0 | 1 | 1 | 0 |
| No. animals surviving after 6 days | 3 | 2 | 5 | 3 | 2 | 2 | 2 | 3 | 1 |

TABLE 24

VIRUS: Influenza, Ann Arbor
Host: Mouse
Dose Schedule: −24; +24, +72
Route of Administration: Oral

| Compound 1-(sec-butylideneamino)- guanidine, nitrate | Total Dose Administered to the Animal. | | | | | | |
|---|---|---|---|---|---|---|---|
| | 300 µg | 30 µg | 3 µg | 300 ng | 30 ng | 3 ng | Control |
| Survivors | 0 | 2 | 0 | 2 | 0 | 0 | 0 |

TABLE 24-continued

VIRUS: Influenza, Ann Arbor
Host: Mouse
Dose Schedule: −24; +24, +72
Route of Administration: Oral

| Compound 1-(sec-butylideneamino)-guanidine, nitrate | Total Dose Administered to the Animal | | | | | | Control |
|---|---|---|---|---|---|---|---|
| | 300 μg | 30 μg | 3 μg | 300 ng | 30 ng | 3 ng | |
| No. animals surviving when 100% of controls are dead | 0 | 2 | 0 | 3 | 0 | 0 | 0 |
| No. animals surviving after 7 days | 0 | 2 | 0 | 3 | 1 | 0 | ½ |

TABLE 25

VIRUS: Influenza, Ann Arbor
Host: Mouse
Dose Schedule: −24; +24, +48
Route of Administration: Oral

| Compound acetoacetic acid, ethyl ester, thiosemicarbazone | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | 0 | 0 | 0 | 0 | 0 | 0 | 0 | 0 | 0 | 0 |
| No. animals surviving when 100% of controls are dead | 1 | 3 | 3 | 2 | 2 | 3 | 2 | 2 | 5 | 0 |
| No. animals surviving after 5 days | 5 | 7 | 8 | 6 | 4 | 5 | 5 | 4 | 8 | 3 |

TABLE 26

VIRUS: Influenza, Ann Arbor
Host: Mouse
Dose Schedule: −24; +24, +72
Route of Administration: Oral

| Compound 1,2-dimethylhydrazine, dihydrochloride | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | 0 | 0 | 0 | 0 | 0 | 1 | 0 | 0 | 1 | 0 |
| No. animals surviving when 100% of controls are dead | 0 | 2 | 2 | 1 | 2 | 1 | 2 | 1 | 4 | 0 |
| No. animals surviving after 6 days | 3 | 6 | 4 | 3 | 5 | 3 | 3 | 2 | 6 | 2½ |

TABLE 27

VIRUS: Influenza, Ann Arbor
Host: Mouse
Dose Schedule: −24; +24, +72
Route of Administration: Oral

| Compound 1,1-dimethylhydrazine | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | 0 | 0 | 1 | 0 | 0 | 0 | 1 | 0 | 0 | 0 |
| No. animals surviving when 100% of controls are dead | 1 | 1 | 1 | 0 | 2 | 1 | 3 | 0 | 3 | 0 |
| No. animals surviving after 6 days | 2 | 3 | 1 | 2 | 3 | 2 | 3 | 3 | 5 | 2½ |

TABLE 28

VIRUS: Influenza, Ann Arbor
Host: Mouse
Dose Schedule: −24; +24, +72
Route of Administration: Oral

| Compound Methylhydrazine | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | * | 0 | 1 | 0 | 0 | 1 | 1 | 0 | 1 | 0 |
| No. animals surviving when 100% of controls are dead | * | 0 | 2 | 0 | 0 | 1 | 2 | 1 | 2 | 0 |
| No. animals surviving after 6 days | * | 1 | 3 | 3 | 1 | 4 | 3 | 3 | 2 | 2½ |

* Toxic

TABLE 29

VIRUS: Influenza, Ann Arbor
Host: Mouse
Dose Schedule: −24, +24, +48
Route of Administration: Oral

| Compound 2-indanone, thiosemicarbazone | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | * | 0 | 0 | 1 | 1 | 0 | 0 | 0 | 1 | 0 |
| No. animals surviving when 100% of controls are dead | * | 2 | 5 | 2 | 1 | 2 | 1 | 2 | 4 | 0 |
| No. animals surviving after 5 days | * | 6 | 8 | 8 | 8 | 9 | 5 | 8 | 8 | 3 |

TABLE 30

VIRUS: Influenza, Ann Arbor
Host: Mouse
Dose Schedule: −24, +24, +48
Route of Administration: Oral

| Compound cyclopentanone, 3-thio-4-O-tolylsemicarbazone | Total Dose Administered to the Animal | | | | | | | | | Control |
|---|---|---|---|---|---|---|---|---|---|---|
| | 3 mg | 300 μg | 30 μg | 3 μg | 300 ng | 30 ng | 3 ng | 300 pg | 30 pg | |
| Survivors | 0 | 0 | 0 | 0 | 0 | 1 | 0 | 0 | 0 | 0 |
| No. animals surviving when 100% of controls are dead | 3 | 4 | 1 | 2 | 1 | 5 | 3 | 5 | 3 | 0 |
| No. animals surviving after 5 days | 8 | 9 | 5 | 6 | 6 | 9 | 9 | 9 | 6 | 3 |

EXAMPLE 4

The following example illustrates the effect of the compounds of this invention on Influenza PR 8 virus. The results are shown in Tables 31–38.

The effect of the hydrazine derivatives on Influenza PR 8 virus was studied in mice. This strain of Influenza seems somewhat more resistant to all of the drugs than the Ann Arbor strain. Nevertheless in Table 31 with no pretreatment, the effect is seen in which only animals that survive are affected, all other animals dying at the same time as the controls, whereas Tables 32 and 33 show that under more optimal conditions with pretreatment, more of the treated animals lived longer than the controls.

Thiosemicarbazone was administered to animals infected with Influenza virus in their drinking water. (Table 34). It is striking that a significant number of survivors were observed when the drug was administered for only a period of 48 hours; 24 hours pre- and 24 hours post-infection. Also at a single dose level there were significant survivors when the animals were allowed access to the drug for only a 24 hour period post-infection.

TABLE 31

Virus: Influenza, PR 8
Dose Schedule: No pre-infection; +30, +72 post-infection.
Route of Administration: Intravenous.
Host: Mouse

| Compound | | Total Dose Administered to the Animal in Micrograms. | | | |
|---|---|---|---|---|---|
| | | 20 | 2 | .2 | Control |
| 2-butanone, thiosemicarbazone | Survivors | 3 | 3 | 2 | 1 |
| | No. animals surviving when 18/20 of controls are dead | 3 | 3 | 2 | 1 |
| | No. animals surviving after 9 days | 3 | 3 | 2 | 1 |

TABLE 32

Virus: Influenza, PR 8
Dose Schedule: −24 pre-infection; +3, +24, +72 post-infection.
Route of Administration: Oral.
Host: Mouse

| Compound | | Total Dose Administered to the Animal in Micrograms. | | | | | | |
|---|---|---|---|---|---|---|---|---|
| | | .5 | .05 | .005 | .0005 | .00005 | .000005 | Control |
| hydrazine, hydrate | Survivors | 1 | 1 | 1 | 2 | 4 | 2 | 0 |
| | No. animals surviving when 18/20 of controls are dead | 1 | 1 | 1 | 3 | 4 | 2 | 1 |
| | No. animals surviving after 8 days | 2 | 3 | 2 | 3 | 5 | 4 | 2½ |
| semicarbazide | Survivors | 1 | 4 | 0 | 0 | 0 | 0 | 0 |
| | No. animals surviving when 18/20 of controls are dead | 3 | 4 | 0 | 0 | 0 | 2 | 1 |
| | No. animals surviving after 8 days | 3 | 4 | 0 | 1 | 0 | 2 | 2½ |

TABLE 33

Virus: Influenza PR 8 Virus
Dose Schedule: −49 pre-infection: +4, +48, +96 post-infection.
Route of Administration: Oral
Host: Mouse

| Compound | | Total Dose Administered to the Animal in Micrograms | | | | |
|---|---|---|---|---|---|---|
| | | .005 | .0005 | .00005 | .000005 | Control |
| 2-butanone, thiosemicarbazone | Survivors | 2 | 1 | 4 | 1 | 0 |
| | No. animals surviving after 100% of controls are dead | 2 | 1 | 4 | 2 | 0 |
| | No. animals surviving after 7 days | 2 | 3 | 8 | 4 | 1½ |
| hydrazine, hydrate | Survivors | 2 | 1 | 0 | 2 | 0 |
| | No. animals surviving when 100% of controls are dead | 2 | 1 | 0 | 4 | 0 |
| | No. animals surviving after 7 days | 5 | 2 | 0 | 4 | 1½ |
| semicarbazide | Survivors | 0 | 0 | 2 | 0 | 0 |
| | No. animals surviving when 100% of controls are dead | 0 | 0 | 0 | 0 | 0 |
| | No. animals surviving after 7 days | 1 | 1 | 3 | 1 | 1½ |

TABLE 34

Virus: Influenza PR 8
Drug Dissolved in Drinking Water
Animals allowed to drink ad lib for 24 hours pre- and 24 hours post-infection.
Host: Mouse

| Compound | | Concentration of Compound in Water in Mg/ml | | | | |
|---|---|---|---|---|---|---|
| | | 10 | 5 | 0.5 | .05 | Control |
| 2-butanone, thiosemicarbazone | Survivors | 2 | 3 | 1 | 3 | 0 |
| | No. animals surviving when 100% of controls | | | | | |

TABLE 34-continued

Virus: Influenza PR 8
Drug Dissolved in Drinking Water
Animals allowed to drink ad lib for 24 hours pre- and 24 hours post-infection.
Host: Mouse

|  |  |  |  |  |  |
|---|---|---|---|---|---|
| are dead | 2 | 3 | 2 | 3 | 0 |
| No. animals surviving after 8 days | 4 | 3 | 2 | 4 | 1 |

Same as above except animals were allowed access to the drug for 24 hours post-infection only.

| 2-butanone, Survivors |  | 0 | 3 | 0 |  |
|---|---|---|---|---|---|

Virus: Influenza PR 8
Drug Dissolved in Drinking Water
Animals allowed to drink ad lib for 24 hours pre- and 24 hours post-infection.
Host: Mouse

| carbazone | No. animals surviving when 100% of controls are dead | 0 | 3 | 0 |
|---|---|---|---|---|
|  | No. animals surviving after 8 days | 1 | 3 | 1 |

TABLE 35

Virus: Influenza, PR 8
Dose Schedule: −144, −96, −48 pre-infection; +4, +48, +96 post infection.
Route of Administration: Oral.
Host: Mouse

| Compound |  | Total Dose Administered to the Animal in Micrograms | | | | |
|---|---|---|---|---|---|---|
|  |  | .005 | .0005 | .00005 | .000005 | Control |
| 2-butanone, thiosemi-carbazone | Survivors | 0 | 1 | 4 | 1 | ½ |
|  | No. animals surviving when 19/20 of controls are dead | 0 | 1 | 4 | 2 | ½ |
|  | No. animals surviving after 8 days | 0 | 3 | 4 | 3 | 1 |

TABLE 36

Virus: Influenza, PR 8 Virus
Dose Schedule: −21 pre-infection; +3, +24, +72 post-infection.
Route of Administration: Oral.
Host: Mouse

| Compound |  | Total Dose Administered to the Animal in Micrograms. | | | | | | | |
|---|---|---|---|---|---|---|---|---|---|
|  |  | 5 | .5 | .05 | .005 | .0005 | .00005 | .000005 | .0000005 | Control |
| Isoniazid | Survivors | 2 | 1 | 1 | 1 | 0 | 0 | 0 | 0 | 0 |
|  | No. animals surviving when 100% controls are dead | 2 | 1 | 0 | 1 | 0 | 0 | 1 | 0 | 0 |
|  | No. animals surviving after 7 days | 5 | 2 | 2 | 1 | 0 | 0 | 2 | 1 | 1 |

TABLE 37

Virus: Influenza PR 8 Virus
Host: Mouse
Dose Schedule: −24 pre-infection; +4, +24, +72 post-infection.
Route of Administration: Oral and subcutaneous

| Compound |  | Total Dose Administered to the Animals in Micrograms. | | | | |
|---|---|---|---|---|---|---|
|  |  | .005 | .0005 | .00005 | .000005 | Control |
| Route of Administration: Oral | | | | | | |
| 2-butanone, thiosemi-carbazone | Survivors | 1 | 1 | 2 | 0 | 0 |
|  | No. animals surviving when 100% of controls are dead | 1 | 1 | 3 | 3 | 0 |
|  | No. animals surviving after 6 days | 2 | 2 | 5 | 6 | 2½ |
| Route of Administration: Subcutaneous | | | | | | |
| 2-butanone, thiosemi-carbazone | Survivors | 0 | 1 | 0 | 0 | 0 |
|  | No. animals surviving when 100% of controls are dead | 1 | 1 | 0 | 1 | 0 |
|  | No. animals surviving after 6 days | 3 | 1 | 3 | 2 | 2½ |

TABLE 38

Virus: Influenza, PR 8
Host: Mouse
Dose Schedule: −24 pre-infection; +24 post-infection.
Route of Administration: Oral.

| Compound | | Total Dose Administered to the Animal in Micrograms. | | | | | | |
|---|---|---|---|---|---|---|---|---|
| | | 50 | 5 | .5 | .05 | .005 | .0005 | Control |
| hydrazine, hydrate | Survivors | 0 | 0 | 1 | 0 | 3 | 1 | 0 |
| | No. animals surviving when 100% of controls are dead | 0 | 0 | 1 | 0 | 3 | 1 | 0 |
| | No. animals surviving after 10 days | 1 | 1 | 1 | 0 | 3 | 1 | 1 |

EXAMPLE 5

The following example illustrates the effect of the test compounds on Influenza B Massachusetts virus. The results are shown in Tables 39 and 40.

The activity of four compounds on Influenza B Mass. was tested in mice. It is evident from Tables 39 and 40 that the test compounds have activity at the geometric mean survival time level.

Geometric mean survival time is the nth route of the n-fold product of the individual survival times of each of the animals where n is the number of animals tested. The foregoing may be expressed by the formula:

$$G.M.S.T. = \sqrt[n]{t_1 \times t_2 \times \ldots \times t_n}$$

TABLE 39

Virus: Influenza B-Mass. Virus
Dose Schedule: −120, −72, −24 pre-infection; +24, +72 post-infection.
Route of Administration: Oral.
Host: Mouse

| Compound | | Total Dose Administered to the Animal in Micrograms | | | | | | |
|---|---|---|---|---|---|---|---|---|
| | | .5 | .05 | .005 | .0005 | .00005 | .000005 | Control |
| 2-butanone, thiosemi-carbazone | Survivors | 1 | 0 | 0 | 0 | 2 | 2 | 0 |
| | No. animals surviving when 100% controls are dead | 4 | 2 | 0 | 1 | 3 | 3 | 0 |
| | No. animals surviving after 5 days | 5 | 4 | 4 | 7 | 8 | 6 | 2 |
| Isoniazid | Survivors | 0 | 0 | 0 | 0 | 0 | 0 | 0 |
| | No. animals surviving when 100% controls are dead | 0 | 1 | 1 | 2 | 1 | 0 | 0 |
| | No. animals surviving after 5 days | 3 | 3 | 5 | 3 | 2 | 3 | 2 |
| semicar-bazide | Survivors | 0 | 0 | 0 | 0 | 0 | 0 | 0 |
| | No. animals surviving when 100% controls are dead | 1 | 1 | 3 | 1 | 0 | 0 | 0 |
| | No. animals surviving after 5 days | 4 | 6 | 6 | 3 | 3 | 3 | 2 |

TABLE 40

VIRUS: Influenza - B-Mass.
Host: Mouse
Dose Schedule: −24; +24, +72, +100
Route of Administration: Oral

| Compound | Total Dose Administered to the Animal | | | | | | |
|---|---|---|---|---|---|---|---|
| aminoguanidine, bicarbonate | 4µg | 400ng | 40ng | 4ng | 400pg | 40pg | Control |
| Survivors | 1 | 1 | 1 | 0 | 2 | 0 | 0 |
| No. animals surviving when, 100% of controls are dead | 1 | 1 | 2 | 1 | 2 | 0 | 0 |
| No. animals surviving | | | | | | | |

TABLE 40-continued

VIRUS: Influenza - B-Mass.
Host: Mouse
Dose Schedule: −24; +24, +72, +100
Route of Administration: Oral

| Compound | Total Dose Administered to the Animal | | | | | |
|---|---|---|---|---|---|---|
| aminoguanidine, bicarbonate | 4μg | 400ng | 40ng | 4ng | 400pg | 40pg | Control |
| after 7 days | 3 | 3 | 7 | 4 | 4 | 2 | 1 |

EXAMPLE 6

The following example illustrates the effect of the test compounds on Influenza B Maryland virus. The results are shown in Table 41. The table shows that 1-methylindole-2,3-dione,3-thiosemicarbazone (methisazone) is active against Influenza B Maryland virus.

TABLE 41

VIRUS: Influenza, B Maryland
Host: Mouse
Dose Schedule: −144, −96, −48 pre-infection; +3, +48, +96 post-infection.
Route of Administration: Oral.

| Compound | Total Dose Administered to the Animal. | | | | |
|---|---|---|---|---|---|
| 1-methylindole-2,3-dione,3-thiosemicarbazone (Methisazone) | 6μg | 600 ng | 60 ng | 6 ng | Control |
| Survivors | 1 | 2 | 2 | 2 | 1 |
| No. animals surviving when 18/20 of controls are dead | 4 | 2 | 4 | 4 | 1 |
| No. animals surviving after 8 days | 5 | 4 | 8 | 5 | 2½ |

EXAMPLE 7

The following example shows the effect of the compounds of this invention on Columbia SK Polio virus in mice. The experiments were done many weeks before optimal conditions of dosage and treatment were known. There are two instances of a statistically significant geometric mean survival time for thiosemicarbazone. The compounds are unequivocally active against this virus, but its actual degree of sensitivity has not been determined. The results are shown in Table 42.

TABLE 42

VIRUS: Columbia SK Polio
Dose Schedule: −24 pre-infection; +3, +24 post-infection.
Route of Administration: Subcutaneous.
Host: Mouse

| Compound | | Total Dose Administered to the Animal. | | | |
|---|---|---|---|---|---|
| | | 300 ng | 30ng | 3 ng | Control |
| 2-butanone thiosemicarbazone | Survivors | 1 | 0 | 0 | 0 |
| | No. animals surviving when 100% of controls are dead | 2 | 3 | 3 | 0 |
| | No. animals surviving after 5 days | 6 | 8 | 7 | 3 |

EXAMPLE 8

The following example illustrates the effect of the compounds of the invention on Mengo virus in mice. The results are illustrated in Table 43. It is evident that there is a protective effect on the mouse hosts.

TABLE 43

Virus: Mengo Virus
Host: Mouse
Dose Schedule: −24 pre-infection; +24, +72 post-infection.
Route of Administration: Oral.

| Compound | | Total Dose Administered to the Animal in Micrograms. | | | | | |
|---|---|---|---|---|---|---|---|
| | | .005 | .0005 | .00005 | .000005 | .0000005 | Control |
| Thiosemicarbazide | Survivors | 0 | 0 | 1 | 1 | 0 | 0 |
| | No. animals surviving when 100% of controls are dead | 0 | 0 | 2 | 2 | 1 | 0 |
| | No. animals surviving after 6 days | 1 | 1 | 5 | 2 | 1 | 1 |

EXAMPLE 9

The following example illustrates the effect of the compounds of the invention on Vaccinia virus. The results are shown in Table 44. The effect of the hydrazine compounds on Vaccinia virus was studied in the mouse tail. The virus was administered intravenously into the tail vein of the mouse and the degree of swelling and vessicle formation in the treated animals was compared with the controls. Table 44 shows that there is a statisticaly significant difference between many of the treated and the control animals. All of these animals were held for 21 days, and there was no evidence of a recurrence of lesions such as was seen in the preliminary studies on Vaccinia in rabbits. (Example 11). In earlier tests done under less optimal conditions there was evidence of recurrence of lesions on the tails at about the 14th or 15th day.

TABLE 44

Virus: Vaccinia IHD
Pre-treatment administered intravenously.
Post-treatment administered orally.
Host: Mouse

| Compound | Total Dose | Statistical Significance of Tail Lesions on Days | | | | | | | | | |
|---|---|---|---|---|---|---|---|---|---|---|---|
| | | 5 | 6 | 7 | 8 | 10 | 11 | 12 | 14 | 17 | 21 |
| Thio-semicar-bazide | 10ng | NS | NS | NS | NS | NS | NS | <.05 | <.05 | <.05 | <.05 |
| | 100 | NS | NS | NS | <.05 | <.01 | <.01 | <.01 | <.01 | <.01 | <.01 |
| | 1 μg | <.01 | <.01 | <.01 | <.01 | <.01 | <.01 | <.01 | <.01 | <.01 | <.01 |
| | 10 | NS | <.01 | NS | NS | <.05 | <.01 | <.01 | <.01 | <.01 | <.01 |
| 2-buta-none, thiose-micar-bazone | 10ng | <.05 | <.01 | <.05 | NS | <.01 | <.01 | <.01 | <.01 | <.01 | <.01 |
| | 100 | <.05 | <.01 | <.01 | <.01 | <.01 | <.01 | <.01 | <.01 | <.01 | <.01 |
| | 1.0μg | <.01 | <.01 | <.05 | <.01 | <.01 | <.01 | <.01 | <.01 | <.01 | <.01 |
| | 10 | NS | <.01 | <.05 | <.05 | <.01 | <.05 | <.05 | <.05 | <.01 | <.01 |
| hydra-zine | 10ng | NS | <.01 | <.05 | NS | NS | <.01 | <.01 | <.01 | <.01 | <.01 |
| | 100 | <.05 | <.01 | <.01 | <.05 | <.01 | <.01 | <.01 | <.01 | <.01 | <.01 |
| | 1.0μg | NS | NS | NS | NS | <.01 | <.01 | <.01 | <.01 | <.01 | <.01 |
| | 10 | NS | NS | NS | NS | <.05 | <.01 | <.01 | <.01 | <.01 | <.01 |
| semicar-bazide, hydro-chloride | 10ng | NS | <.01 | NS | NS | NS | <.05 | <.05 | NS | <.05 | NS |
| | 100 | NS | NS | <.05 | NS | NS | <.05 | <.05 | <.05 | <.01 | <.01 |
| | 1.0μg | NS | <.01 | NS | <.01 | <.01 | <.01 | <.01 | <.01 | <.01 | <.05 |
| | 10 | NS | NS | <.01 | NS | <.05 | <.01 | <.01 | <.01 | <.01 | <.05 |

EXAMPLE 10

The following example illustrates the effect of the compounds of this invention on Neurovaccinia. Several tests of the hydrazines on Neurovaccinia in mice have been carried out. In these tests the virus challenge was intracerebral and several of the compounds of this invention were administered either subcutaneously or orally. This is an overwhelming infection and very few compounds have ever been found to show any significant effect. In three instances, thiosemicarbazide, at a single dose level has shown one surviving animal, and it was found that this computed as statistically significant at geometric mean survival time level. The results are shown in Table 45.

EXAMPLE 11

The following example illustrates the effect of the compounds of this invention on Vaccinia virus. The results are shown in Table 46. A few experiments were performed studying the influence of thiosemicarbazone and thiosemicarbazide on the development of pox formation from Vaccinia virus in the scarified rabbit skin. An experiment on thiosemicarbazone showed very striking effects of the drug on the pox formation, there being dramatic reduction and even elimination of all pox formation over several dilutions. In a few instances, but not all, after another 24 hours there was some evidence of recurrence of the pox. This experiment was repeated twice, unsuccessfully. The preparations used in the test were analyzed, and it was found that the submission sample of thiosemicarbazone was contaminated with a small percentage of thiosemicarbazide. The preparations of the latter thiosemicarbazone that were injected into the rabbits in the case of the unsuccessful experiments contained, for some unexplained reason, no detectable thiosemicarbazide. Thiosemicarbazide was then tested repeatedly with highly significant and reproducible protective effects. It has not yet been determined whether it was the presence of the contaminant thiosemicarbazide in the preparations of thiosemicarbazone that gave protective effects or some other phenomena. Table 46 gives the results of three tests done consecutively on thiosemicarbazide and in each instance it was found that when the rabbit was

TABLE 45

VIRUS: Neurovaccinia
Dose Schedule: −24 pre-infection; +24, +72 post-infection.
Route of Administration: Intraperitoneal.
Host: Mouse

| Compound | | Total Dose Administered to the Animal. | | | |
|---|---|---|---|---|---|
| | | .75 μg | .075 μg | .0075μg | Control |
| semicarbazide hydrochloride | Survivors | 0 | 1 | 0 | 0 |
| | No. animals surviving when 100% of controls are dead | 1 | 1 | 0 | 0 |
| | No. animals surviving after 6 days | 1 | 1½ | ½ | ½ | given either 0.25 or 2.5 μg/kg there was a highly significant diminution in the vacccinia pox formation. In most instances after a second 24 hour period some recurrence of the pox was evident.

All of these experiments were carried out with the drug administerd intraperitoneally, a route that is now known to be the least efficacious in the mouse. It remains to be determined whether more optimal conditions of administration will give more uniform, consistent and permanent effects on Vaccinia in the rabbit.

Vaccinia Virus in Rabbits

On three occasions identical experiments were carried out in which rabbits were injected with thiosemicarbazide, 24 hours before vaccination, vaccinated on the second day at which time a second dose of drug was given, and on the third day a third dose of drug was administered, all intraperitoneally. The results of the test were read on the 5th day. The results obtained were as follows, the figures being aproximate percentage confluency of the pox on the scarified area.

TABLE 46

| μg/kg | Test 1 | Test 2 | Test 3 | (Duplicate Experiments) |
|---|---|---|---|---|
| Control 1 | 80% | 95% | 80 | 95 |
| Control 2 | 90% | 85% | 70 | 90 |
| 250 | 80% | | | |
| 25 | 80% | 10% | | |
| 2.5 | 50% | 80% | 30 | 30 |
| | | | 20 | 20 |
| 0.25 | 10% | 10% | 30 | — |
| | | | 40 | — |
| 0.025 | 5% | 5% | 75 | 75 |
| | | | 90 | 80 |
| 0.0025 | 2% | 80% | 85 | 75 |
| | | | 85 | 60 |
| 0.00025 | | 40% | | |
| 0.000025 | | 25% | | |
| 0.0000025 | | 85% | | |

A T test on these data resulted in the following findings:

| Dose 0.025 | T = 1.99;NS |
|---|---|
| Dose 0.25 | T = 6.437;S<.01 |
| Dose 2.5 | T = 4.911;S<.01 |

At the 0.25 and the 2.5 μg/kg levels it is very highly significant, far less than 0.01. The 2.5 μg/kg dose corresponds to 50 nanograms per mouse (ng/mouse), and the 0.25 μg/kg dose corresponds to 5 ng/mouse.

EXAMPLE 12

The following example illustrates the effect of the compounds of the invention in tissue cultures. The compounds were tested against Herpes, Influenza and Vaccinia virus in tissue culture using both pre- and post-treatment of the cells, and dilutions down to 0.001 picograms. All tests were negative.

The effect of various concentrations of thiosemicarbazide and semicarbazide on Vaccinia pox formation on the chorioallantoic membrane of fertile eggs was studied. No effect on pox formation on the membrane could be observed. This is in accord with other experimentation because pox formation on membranes is actually a specialized form of tissue culture and no activity has been demonstrable in tissue culture.

Several of these compounds were tested for viricidal activity, and none was demonstrated.

EXAMPLE 13

The following example illustrates the optimal routes of administration of the compounds of this invention. The results are shown in Tables 11, 14, 34 and 47.

A test on Influenza PR 8 virus administered in drinking water was done and the results are shown in table 34. It is clearly evident that animals receiving thiosemicarbazone for 24 hours pre- and 24 hours post-infection in drinking water were significantly protected against death. Administration of drug for only 24 hours post-infection provided significant protection at a single dose level.

Table 47 shows a comparison of oral, subcutaneous and intraperitoneal administration of thiosemicarbazide against Influenza PR 8 virus. It is evident here that in this experiment intraperitoneal administration gave almost no protection, whereas oral and subcutaneous administration was effective and gave comparable results. It has been found that with the subcutaneous route of administration a larger dose of drug is required than when the oral route of administration is used.

Table 11 shows the effect of oral and subcutaneous administration of semicarbazide on Influenza, Ann Arbor virus. Again, it is clearly evident that oral administration is better with significant protection over a wide range, 10 survivors being observed over four log doses whereas under identical conditions with subcutaneous administration only three animals survived over a four log dose range.

Table 14 shows the results of a study of oral and subcutaneous administration of aminoguanidine on Influenza Ann Arbor infections of mice. On oral administration at a high dose, 50% of the treated animals survived, and the effect is spread over several dose ranges from 0.3 to 30 μg/dose. In this experiment, with subcutaneous administration, 50% survival was found only at one dose level, and not spread as seen above. These experiments clearly indicate that oral is the preferred route of administration.

TABLE 47

Virus: Influenza, PR 8 Virus
Dose Schedule: −24 pre-infection; +3, +24 post-infection.
Route of Administration: Oral, Subcutaneous, Intraperitoneal
Host: Mouse

| Compound: Thiosemicarbazide | | Total Dose Administered to the Animal in Micrograms | | | | | |
|---|---|---|---|---|---|---|---|
| | | 5 | .5 | .05 | .005 | .0005 | Control |
| ORAL | | | | | | | |
| | Survivors | 1 | 0 | 1 | 3 | 2 | 0 |
| | No. animals surviving when 100% of controls are dead | 1 | 0 | 1 | 3 | 2 | 0 |
| | No. animals surviving after 8 days | 3 | 1 | 2 | 3 | 2 | 1 |
| SUBCUTANEOUS | Survivors | 3 | 2 | 2 | 0 | 0 | 0 |

TABLE 47-continued

Virus: Influenza, PR 8 Virus
Dose Schedule: −24 pre-infection; +3, +24 post-infection.
Route of Administration: Oral, Subcutaneous, Intraperitoneal
Host: Mouse

| Compound: Thiosemicarbazide | | Total Dose Administered to the Animal in Micrograms | | | | | |
|---|---|---|---|---|---|---|---|
| | | 5 | .5 | .05 | .005 | .0005 | Control |
| | No. animals surviving when 100% of controls are dead | 3 | 2 | 2 | 1 | 0 | 0 |
| | No. animals surviving after 8 days | 3 | 2 | 2 | 1 | 2 | 1 |
| INTRAPERITONEAL | Survivors | 0 | 0 | 0 | 0 | 1 | 0 |
| | No. animals surviving when 100% of controls are dead | 0 | 0 | 0 | 0 | 2 | 0 |
| | No. animals surviving after 8 days | 1 | 0 | 1 | 2 | 2 | 1 |

EXAMPLE 14

The following example illustrates the optimal dose schedules of the compounds useful in the practice of this invention. The results are shown in Tables 11–14 and 47–50.

The early work on these compounds was done in experiments in which the drugs were administered on a dose schedule of about 24 hours. Table 47 illustrates the effects seen with such a schedule. In the table, on oral administration, the total number of treated animals surviving longer than control animals is somewhat less at all dose levels than that seen with more favorable dose schedules. It has now been found that a treatment schedule with about 48 hour intervals between doses gives somewhat better results. Such a schedule is illustrated in Tables 12–14 and 48.

A few studies have been done in which no pre-treatment was administered. Table 50 shows the results of this on Herpes virus infection, with semicarbazide, and erratic results are evident, although at one dose level 50% of the animals were protected.

Table 49 shows the results of post-infection treatment only on Herpes virus with semicarbazide. In one case treatment was initiated 2 hours after infection, in a second case 4 hours after infection, and in the third case 20 hours post-infection, all with no pre-treatment. When the first drug was administered 2 hours after infection from 20 to 30% of the animals survived at certain dose levels. At 8 hours after infection 2 animals survived, and when treatment was delayed until after 20 hours, only an occasional animal survived. It is striking that even with a 20 hour delay of treatment after infection a protective effect is produced sufficiently great that it is demonstrable by inspection rather than by the use of statistics.

TABLE 48

Virus: Herpes Virus
Dose Schedule: −24 pre-infection; +24, +72, +120 post-infection.
Route of Administration: Oral
Host: Mouse

| Compound | | Total Dose Administered to the Animal in Micrograms | | | | |
|---|---|---|---|---|---|---|
| | | .005 | .0005 | .00005 | .000005 | Control |
| semicarbazide | Survivors | 2 | 2 | 3 | 0 | 0 |
| | No. animals surviving when 100% of controls are dead | 2 | 2 | 3 | 0 | 0 |
| | No. animals surviving after 9 days | 3 | 2 | 3 | 0 | 1½ |

TABLE 49

Virus: Herpes Virus
Host: Mouse
Route of Administration: Oral

| compound: Semicarbazide | | Total Dose Administered to the Animal in Micrograms | | | | |
|---|---|---|---|---|---|---|
| | | .005 | .0005 | .00005 | .000005 | Control |
| Dose Schedule: No pre-infection; +2, +50, +98, +146 post-infection. | | | | | | |
| semicarbazide | Survivors | 3 | 0 | 3 | 2 | 0 |
| | No. animals surviving when 100% of controls are dead | 3 | 0 | 3 | 3 | 0 |
| | No. animals surviving after 8 days | 3 | 0 | 3 | 4 | 1 |
| Dose Schedule: No pre-infection; +8, +56, +105, +152 post-infection. | | | | | | |
| | Survivors | 0 | 2 | 0 | 0 | 0 |
| | No. animals surviving when 100% of controls are dead | 0 | 3 | 0 | 0 | 0 |

TABLE 49-continued

Virus: Herpes Virus
Host: Mouse
Route of Administration: Oral

| compound: Semicarbazide | Total Dose Administered to the Animal in Micrograms | | | | |
|---|---|---|---|---|---|
| | .005 | .0005 | .00005 | .000005 | Control |
| No. animals surviving after 8 days | 1 | 2 | 2 | 1 | 1 |
| Dose Schedule: No pre-infection; +20, +29, +77, +125 post-infection | | | | | |
| Survivors | 1 | 1 | 0 | 1 | 0 |
| No. animals surviving when 100% of controls are dead | 1 | 3 | 1 | 2 | 0 |
| No. animals surviving after 8 days | 1 | 3 | 2 | 2 | 1 |

TABLE 50

Virus: Herpes Virus
Dose Schedule: No pre-infection; +1, +49, +96, +120 post-infection.
Route of Administration: Oral
Host: Mouse

| Compound: Semicarbazide | Total Dose Administered to the Animal in Micrograms | | | | |
|---|---|---|---|---|---|
| | .005 | .0005 | .00005 | .000005 | Control |
| Survivors | 2 | 0 | 5 | 1 | 0 |
| No. animals surviving when 100% of controls are dead | 2 | 0 | 5 | 1 | 0 |
| No. animals surviving after 9 days | 2 | 1 | 5 | 1 | 1½ |

EXAMPLE 15

The following example illustrates the effect of prolonged pretreatment on the activity of the compounds useful in the practice of this invention against viruses. The results are shown in Tables 2, 3, 5, 51 and 52.

Several experiments were undertaken to demonstrate whether pretreatment for as much as 6 days influenced the antiviral effect of the drugs. Table 51 shows the influence of this on an Ann Arbor Influenza infection. It is evident that of the three drugs studied, all were effective with this prolonged administration prior to infection. This indicates that a triggering mechanism similar to Interferon induction is not at play in this phenomenon and it is believed indicates that the compounds of this invention are protective against viral infections on prolonged administration. Tables 3 and 39 illustrate the effect of at least two preinfection immunizations about 48 hours apart, and continuing at about 48 hour intervals for at least two post infection doses, the infection being 24 hours after the preinfection dose. A pronounced and significant effect is demonstrable on five of the hydrazine derivatives. Table 3 illustrates a schedule where the doses were given —96 and —48 hours preinfection, and the animals infected and dosed at about the same time followed by two more 48 hour drug administrations. It is evident that with semicarbazide there is very pronounced protection and quite significant protection with thiosemicarbazide.

TABLE 51

Virus: Influenza, Ann Arbor
Dose Schedule: —140, —96, —48 pre-infection; 0, +48, +96 post-infection.
Route of Administration: Oral.
Host: Mouse

| Compound | | Total Dose Administered to the Animal in Micrograms. | | | |
|---|---|---|---|---|---|
| | | .5 | .05 | .005 | Control |
| semicarbazide | Survivors | 1 | 1 | 1 | 0 |
| | No. animals surviving when 100% of controls are dead | 1 | 1 | 1 | 0 |
| | No. animals surviving after 8 days | 3 | 2 | 4 | 2½ |
| thiosemicarbazide | Survivors | 0 | 2 | 1 | 0 |
| | No. animals surviving when 100% of controls are dead | 2 | 3 | 1 | 0 |
| | No. animals surviving after 8 days | 7 | 5 | 2 | 2½ |
| Isoniazid | Survivors | 2 | 2 | 2 | 0 |
| | No. animals surviving when 100% of controls are dead | 2 | 2 | 2 | 0 |
| | No. animals surviving after 8 days | 6 | 5 | 5 | 2½ |

TABLE 52

Virus: Herpes-Virus
Dose Schedule: —50, —25 pre-infection; +17, +65, +114 post-infection
Route of Administration: Oral
Host: Mouse

| Compound | | Total Dose Administered to the Animal in Micrograms | | | | | |
|---|---|---|---|---|---|---|---|
| | | 5 | .5 | .05 | .005 | .0005 | Control |
| Hydrazine Sulfate | Survivors | 2 | 1 | 0 | 4 | 3 | 0 |

TABLE 52-continued

Virus: Herpes-Virus
Dose Schedule: −50, −25 pre-infection; +17, +65, +114 post-infection
Route of Administration: Oral
Host: Mouse

| Compound | Total Dose Administered to the Animal in Micrograms | | | | | |
|---|---|---|---|---|---|---|
| | 5 | .5 | .05 | .005 | .0005 | Control |
| No. animals surviving when 100% of controls are dead | 2 | 2 | 1 | 4 | 3 | 0 |
| No. animals surviving after 9 days | 3 | 3 | 1 | 4 | 3 | ½ |

The activity of 2-butanone thiosemicarbazone is shown in Tables 4, 10, 31, 33–35, 37, 39, 42 and 44. The tables illustrate the activity of the compound against Influenza, Vaccinia, Columbia SK polio and Herpes virus infections. It is one of the most active compounds that has been studied to date. It appears to be the most active of the compounds tested on Vaccinia in the mouse tail.

Thiosemicarbazide has been found to be active against Influenza PR 8, Vaccinia in the mouse tail, Mengo virus, Herpes virus in mice and eggs, Influenza virus, and Vaccinia virus in rabbits as shown in Tables 1–4, 10, 43, 44, 46, 47 and 51. The variability of some experiments from test to test is illustrated. It appears not to be as effective against many or most of these viruses as some of the other compounds of this invention. It is also active on Neurovaccinia virus in mice.

Semicarbazide hydrochloride has been shown to be effective against Influenza PR 8 virus, Vaccinia virus in the mouse tail, Herpes virus in eggs, Herpes virus in Mice, Neurovaccinia, and Influenza Ann Arbor virus as shown in Tables 1–3, 6, 10, 11, 17, 32, 33, 39, 44, 45, and 48–51. It is quite active on Herpes virus, but may be less active on Influenza virus, Ann Arbor, and has even less activity on Influenza PR 8.

Hydrazine hydrate has been shown to be active on Influenza PR 8, Vaccina in the mouse tail, Herpes in eggs, Herpes in mice, and Influenza Ann Arbor as shown in Tables 1, 8, 10, 12, 13, 15, 32, 33, 38, 44 and 52.

Isoniazid has been tested and found to be active against Influenza PR 8, Influenza Ann Arbor, Influenza B Mass., and Herpes virus as shown in Tables 4, 7, 9, 16, 17, 36, 39 and 51. The activity of this compound appears to be spread over a wide dose range and of reasonable degree of activity. The maximum protective effect that has been found is that 30% of the treated animals survived. In several instances as may be seen from the tables, animals show a prolongation of life well beyond the controls, indicating significant intrinsic activity.

Methisazone has been tested against Herpes virus, Influenza Ann Arbor and Influenza B Maryland, and found to have activity as shown in Tables 5, 7, 9, 15 and 41.

Hydralazine has been tested and found effective against Herpes virus as shown in Tables 5, 7 and 9.

Aminoguanidine bicarbonate has been tested against Influenza virus, Ann Arbor and B Mass., and found to have very pronounced protective effects when administered either orally or subcutaneously as is shown in Tables 14 and 40.

The following compounds have been tested and found effective in oral administration against Influenza Arbor virus as shown in the tables opposite the compound:

| Table | Compound |
|---|---|
| 18 | [(2,6-Dichlorobenzylidine)amino]guanidine acetate |
| 19, 20 | 3-Pentanone, thiosemicarbazone |
| 21, 22 | 2-Pentanone, thiosemicarbazone |
| 23 | Acetone, thiosemicarbazone |
| 24 | 1-(sec-Butylideneamino)guanidine, nitrate |
| 25 | Acetoacetic acid, ethyl ester, thiosemicarbazone |
| 26 | 1,2-Dimethylhydrazine, dihydrochloride |
| 27 | 1,1-Dimethylhydrazine |
| 28 | Methylhydrazine |
| 29 | 2-Indanone, thiosemicarbazone |
| 30 | Cyclopentanone, 3-thio-4-o-tolylsemicarbazone |

The results of tests on other compounds found active are shown in Tables 53–65.

TABLE 53

VIRUS: Influenza, Ann Arbor
Dose Schedule: −24, +24, +72
Route of Administration: Oral
Host: Mouse

| Thiourea | Total Dose Administered to the Animal | | | | | | | | | |
|---|---|---|---|---|---|---|---|---|---|---|
| | 3 mg | 300 µg | 30 µg | 3 µg | 300 ng | 30 ng | 3 ng | 300 pg | 30 pg | Control |
| Survivors | 0 | 1 | 0 | 0 | 0 | 0 | 1 | 0 | 0 | 0 |
| No. animals surviving when 100% of controls are dead | 2 | 4 | 1 | 2 | 2 | 0 | 3 | 2 | 0 | 0 |
| No. animals surviving after 7 days | 5 | 6 | 3 | 7 | 2 | 4 | 3 | 4 | 2 | 4 |

TABLE 54

VIRUS: Influenza, Ann Arbor
Dose Schedule: −24; +24, +72
Route of Administration: Oral
Host: Mouse

| Methylhydrazine | Total Dose Administered to the Animal | | | | | | | | | Control |
|---|---|---|---|---|---|---|---|---|---|---|
| | 3 mg | 300 µg | 30 µg | 3 µg | 300 ng | 30 ng | 3 ng | 300 pg | 30 pg | |
| Survivors | * | 0 | 1 | 0 | 0 | 1 | 1 | 0 | 1 | 0 |
| No. animals surviving when 100% of controls are dead | * | 0 | 2 | 0 | 0 | 1 | 2 | 1 | 2 | 0 |
| No. animals surviving after 6 days | * | 1 | 3 | 3 | 1 | 4 | 3 | 3 | 2 | 2½ |

* Toxic

TABLE 55

VIRUS: Influenza, Ann Arbor
Dose Schedule: −24; +3, +48, +72
Route of Administration: Oral
Host: Mouse

| Nialamide | Total Dose Administered to the Animal | | | | | | | | Control |
|---|---|---|---|---|---|---|---|---|---|
| | 4 mg | 400 µg | 40 µg | 4 µg | 400 ng | 40 ng | 4 ng | 400 pg | |
| Survivors | 1 | 2 | 5 | 0 | 0 | 0 | 1 | 1 | 0 |
| No. animals surviving when 100% of controls are dead | 1 | 3 | 5 | 0 | 0 | 0 | 1 | 1 | 0 |
| No. animals surviving after 9 days | 2 | 3 | 6 | 2 | 0 | 1 | 2 | 1 | ½ |

TABLE 56

VIRUS: Influenza, Ann Arbor
Dose Schedule: −24, +24, +72
Route of Administration: Oral
Host: Mouse

| 2-Indanone, 4-allylthio-semicarbazone | Total Dose Administered to the Animal | | | | | | | | | Control |
|---|---|---|---|---|---|---|---|---|---|---|
| | 3 mg | 300 µg | 30 µg | 3 µg | 300 ng | 30 ng | 3 ng | 300 pg | 30 pg | |
| Survivors | 1 | 0 | 0 | 0 | 0 | 0 | 0 | 0 | 0 | 0 |
| No. animals surviving when 100% of controls are dead | 2 | 1 | 3 | 1 | 3 | 2 | 2 | 4 | 1 | 0 |
| No. animals surviving after 7 days | 4 | 2 | 6 | 2 | 6 | 6 | 4 | 7 | 4 | 4 |

TABLE 57

VIRUS Influenza, A$_2$, Taiwan
Dose Schedule: Part 1: −48, +1, +48, +72; Part 2: +1, +48, +72
Route of Administration: Oral

| | Compound: Cyclobutanone, thiosemi-carbazone | Total Dose Administered to the Animal | | | | | | Control |
|---|---|---|---|---|---|---|---|---|
| | | 40 µg | 4 µg | 400 ng | 40 ng | 4 ng | .4 ng | |
| −48, +1, +48, +72 Part 1 | Survivors | 1 | 3 | 1 | 3 | 0 | 0 | 1 |
| | No. animals surviving when 18/20 of controls are dead (18/20) | 1 | 3 | 1 | 3 | 0 | 0 | 1 |
| | No. animals surviving after 8 days | 2 | 4 | 3 | 6 | 0 | 1 | 3 |
| | | 30 µg | 3 µg | 300 ng | 30 ng | 3 ng | | |
| No pre; +1, +48, +72 Part 2 | Survivors | 2 | 2 | 3 | 2 | | | 1 |
| | No. animals surviving when 18/20 of controls are dead | 3 | 3 | 3 | 3 | | | 1 |
| | No. animals surviving after 8 days | 4 | 4 | 4 | 5 | | | 3 |

TABLE 58

VIRUS: Influenza A₂, Taiwan
Dose Schedule: −24; +24, +72
Route of Administration: Oral
Host: Mouse

|   |   | Total Dose Administered to the Animal | | | | | | |
|---|---|---|---|---|---|---|---|---|
|   |   | 30μg | 3μg | 300ng | 30ng | 3ng | .3ng | Control |
| * | Survivors | 3 | 4 | 2 | 3 | 3 | 4 | ½ |
|   | No. animals surviving when 19/20 of controls are dead (19/20) | 4 | 5 | 2 | 4 | 3 | 4 | ½ |
|   | No. animals surviving after 8 days | 7 | 5 | 4 | 5 | 4 | 4 | 1½ |
| ** | Survivors | 1 | 5 | 2 | 2 | 2 | 2 | ½ |
|   | No. animals surviving when 19/20 of controls are dead (19/20) | 3 | 5 | 3 | 2 | 3 | 3 | ½ |
|   | No. animals surviving after 8 days | 3 | 6 | 5 | 3 | 4 | 5 | 1½ |
| *** | Survivors | 2 | 3 | 1 | 4 | 1 | 3 | ½ |
|   | No. animals surviving when 19/20 of controls are dead | 3 | 4 | 1 | 5 | 1 | 8 | ½ |
|   | No. animals surviving after 8 days | 3 | 6 | 2 | 5 | 6 | 9 | 1½ |

\* Cyclopentanone, o-tolylthiosemicarbazone
\*\* 3,5-Diamino-6-phenyl-1,2,4-triazine
\*\*\* 5-(1-Adamantyl)-1H-tetrazole

TABLE 59

VIRUS: Influenza A₂, Taiwan
Dose Schedule: −24; +24, +72
Route of Administration: Oral
Host: Mouse

| 5-(1-Adamantyl)-1H-tetrazole | Total Dose Administered to the Animal | | | | | | |
|---|---|---|---|---|---|---|---|
|   | 30μg | 3μg | 300ng | 30ng | 3ng | .3ng | Control |
| Survivors | 2 | 3 | 1 | 4 | 1 | 3 | ½ |
| No. animals surviving when 19/20 of controls are dead | 3 | 4 | 1 | 5 | 1 | 8 | ½ |
| No. animals surviving after 8 days | 3 | 6 | 2 | 5 | 6 | 9 | 1½ |

TABLE 60

VIRUS: Influenza A₂, Taiwan
Dose Schedule: −24; +24, +72
Route of Administration: Oral
Host: Mouse

| 3,5-Diamino-6-phenyl-1,2,4-triazine | Total Dose Administered to the Animal | | | | | | |
|---|---|---|---|---|---|---|---|
|   | 30μg | 3μg | 300ng | 30ng | 3ng | .3ng | Control |
| Survivors | 1 | 5 | 2 | 2 | 2 | 2 | ½ |
| No. animals surviving when 19/20 of controls are dead | 3 | 5 | 3 | 2 | 3 | 3 | ½ |
| No. animals surviving after 8 days | 3 | 6 | 5 | 3 | 4 | 5 | 1½ |

TABLE 61

VIRUS: Influenza, B Mass.
Dose Schedule: −45; +1, +48, +96, +144
Route of Administration: Oral
Host: Mouse

| * Cyclohexanone, thiosemicarbazone; Cyanoacetic Acid oxide** | | Total Dose Administered to the Animal | | | | | | |
|---|---|---|---|---|---|---|---|---|
|   |   | 500ng | 50ng | 5ng | 500pg | 50pg | 5pg | Control |
| * | Survivors | 1 | 5 | 2 | 2 | 2 | 5 | 2 |
|   | No. animals surviving when 16/20 of controls are dead | 1 | 7 | 2 | 2 | 3 | 5 | 2 |
|   | No. animals surviving after 11 days | 2 | 7 | 3 | 2 | 4 | 7 | 4 |
| ** | Survivors | 4 | 3 | 1 | 5 | 4 | 3 | 2 |
|   | No. animals surviving when 16/20 of controls are dead | 4 | 4 | 2 | 5 | 4 | 3 | 2 |

TABLE 61-continued

VIRUS Influenza, B Mass.
Dose Schedule: −45; +1, +48, +96, +144
Route of Administration: Oral
Host: Mouse

| * Cyclohexanone, thiosemicar- bazone; Cyanoacetic Acid oxide** | Total Dose Administered to the Animal | | | | | | |
|---|---|---|---|---|---|---|---|
| | 500ng | 50ng | 5ng | 500pg | 50pg | 5pg | Control |
| No. animals surviving after 11 days | 5 | 4 | 2 | 8 | 4 | 3 | 4 |

TABLE 62

VIRUS: Herpes Simplex
Dose Schedule: −46, +1, +45, +96
Route of Administration: Oral
Host: Mouse

| Adamantyl thiosemicarba- zide | Total Dose Administered to the Animal | | | | | | |
|---|---|---|---|---|---|---|---|
| | 400ng | 40ng | 4ng | 400pg | 40pg | 4pg | Control |
| Survivors | 3 | 2 | 2 | 3 | 1 | 1 | 1 |
| No. animals surviving when 18/20 of controls are dead | 3 | 2 | 2 | 3 | 1 | 1 | 1 |
| No. animals surviving after 9 days | 3 | 2 | 4 | 3 | 2 | 2 | 2 |

Tables 63 and 64 are a summary of the activity of the compounds described herein. Activity at the survival level is indicated with an S. Activity at the increased geometric mean survival time level is indicated with a P for prolongation. Activity in certain specialized tests is indicated by either an A where active, or I where inactive. An N indicates that the test was not performed.

Significance at the survival level was recorded only for those tests on compounds in which two or more animals survived at least three different dose levels or at least three animals survived at a single dose level in tests in which a minimal number of controls survived. Significant prolongation is recorded only where a large number of treated animals survived at the time that almost all of the controls animals were dead. In those instances where a given test has been repeated two or more times, the significance of the most active test is recorded in the chart.

The classes to which the compounds belong may be conveniently summarized as follows:

1 a. Thiosemicarbazone
 b. Substituted thiosemicarbazone
 c. Thiosemicarbazide
2. Semicarbazide
3. Hydrazine
4a. Hydrazide
 b. Substituted hydrazide
5a. Aminoguanidine
 b. Substituted aminoguanidine
6 a. Indazoles
 b. Phthalazine
 c. Triazine
7 b. Tetrazole

TABLE 63

| COMPOUND | Influ- enza A PR 8 | Influ- enza A₁ Ann Arbor | Influ- enza A₂ Taiwan | Influ- enza B Mass. | Influ- enza B Mary- land | Herpes in Mice | Herpes in Eggs | Vac- cinia in Mouse Tail | Vac- cinia in Rab- bits | Neuro- vac- cinia in Mice | Colum- bia SK Polio in Mice | Mengo in Mice | Cox- sackie in Mice |
|---|---|---|---|---|---|---|---|---|---|---|---|---|---|
| Isoniazid | P | S | I | S | P | P | N | N | N | N | N | N | N |
| Nialamide | N | S | N | N | N | N | N | N | N | N | N | N | N |
| Hydralazine | I | I | N | N | P | P | S | N | N | N | N | N | N |
| Adamantyl thiosemicarbazide | N | N | N | N | N | P | N | S | N | N | N | N | N |
| [(2,6-dichlorobenzyl- idene)amino] guanidine | N | P | N | P | N | N | S | N | N | N | N | N | N |
| Thiosemicarbazide | S | P | N | S | S | S | S | S | S | P | P | P | N |
| 2-Butanone, thiosemicarbazone | S | P | S | S | P | S | S | S | I | I | P | P | I |
| 3-Pentanone, thiosemicarbazone | N | P | N | P | N | P | S | N | N | N | N | P | N |
| 2-Pentanone, thiosemicarbazone | N | P | N | N | N | P | N | N | N | N | N | P | N |
| Acetone, thiosemicarbazone | N | P | N | N | N | N | N | N | N | N | N | S | N |
| 1-(sec-Butylidene- amino)quanidine, nitrate | N | P | N | N | N | N | N | N | N | N | N | N | N |
| Acetoacetic acid, ethyl ester, thiosemicarbazone | N | P | N | N | N | N | N | N | N | N | N | N | N |
| Hydrazine sulfate | S | S | N | S | P | S | S | S | N | I | N | N | N |
| Semicarbazide, hydrochloride | S | S | N | P | P | S | S | S | N | P | N | N | N |

TABLE 63-continued

| COMPOUND | Influenza A PR 8 | Influenza A₁ Ann Arbor | Influenza A₂ Taiwan | Influenza B Mass. | Influenza B Maryland | Herpes in Mice | Herpes in Eggs | Vaccinia in Mouse Tail | Vaccinia in Rabbits | Neurovaccinia in Mice | Columbia SK Polio in Mice | Mengo in Mice | Coxsackie in Mice |
|---|---|---|---|---|---|---|---|---|---|---|---|---|---|
| Cyclohexanone, thiosemicarbazone | N | N | N | S | N | N | N | N | N | N | N | N | N |
| Aminoguanidine, bicarbonate | N | S | N | S | N | N | S | N | N | N | N | N | N |
| Methisazone | P | P | N | N | P | S | I | N | N | N | N | N | N |

TABLE 64

| COMPOUND | Influenza A₁ Ann Arbor | Influenza A₂ Taiwan | Influenza B Mass. | Influenza B Maryland | Herpes in Mice | Herpes in Eggs | Vaccinia in Mouse Tail |
|---|---|---|---|---|---|---|---|
| sym-Dimethylhydrazine dihydrochloride | P | N | N | N | N | N | N |
| unsym-Dimethylhydrazine | P | N | N | N | N | N | N |
| Methylhydrazine | P | N | N | N | N | N | N |
| 2-Indanone, thiosemicarbazone | P | N | N | N | N | N | N |
| 2-Indanone, 4-allylthiosemicarbazone | P | P | N | P | N | N | N |
| Cyclopentanone, o-tolylthiosemicarbazone | P | S | N | N | N | N | N |
| 3,5-Diamino-6-phenyl-1,2,4-triazine | N | S | S | N | N | S | N |
| Cyclobutanone, thiosemicarbazone | N | S | P | N | N | S | N |
| Cyanoacetic Acid Hydrazide | N | N | P | N | N | N | N |
| 5-(1-Adamantyl)-1H-tetrazole | P | S | N | N | S | N | S |

EXAMPLE 16

A portion of a commercially available sample of amantadine was recrystalized from isopropanol. The activity of the material against Influenza B Mass. was tested for the sample as obtained, the recrystallized portion, and the mother liquor obtained from recrystallizing the portion. The results are shown below in Table 65. All three were found to be active in the chemoprophylaxis of Influenza B Massachusetts in the dose ranges used. Amantadine has been reported in the literature to be ineffective against Influenza B Massachusetts in larger doses and at different dose schedules. Effective chemoprophylaxis was obtained at doses ranging from 3 nanograms to 9 milligrams per mouse weighing 16 to 20 grams. This is equivalent to a dose of about 150 nanograms to 450 milligrams per kilogram of host body weight. Effective results were obtained at dose schedules of 24 and 48 hours.

TABLE 65

VIRUS: Influenza B Massachusetts
Dose Schedules: −72, −24, +24, +72, +123, +144
Route of Administration: Oral
Host: Mouse

| | | Total Dose Administered to the Animal | | | | | | |
|---|---|---|---|---|---|---|---|---|
| | | 6 mg | 600 μg | 60 μg | 6 μg | 600 ng | 60 ng | Control |
| Commercial amantadine | Survivors | 2 | 5 | 2 | 5 | 3 | 0 | 0 |
| | No. animals surviving when 100% of controls are dead | 2 | 5 | 2 | 5 | 3 | 0 | 0 |
| | No. animals surviving after 11 days | 4 | 5 | 3 | 7 | 3 | 3 | 1½ |
| Recrystallized amantadine | Survivors | 4 | 2 | 2 | 5 | 3 | 2 | 0 |
| | No. animals surviving when 100% of controls are dead | 4 | 2 | 2 | 5 | 3 | 2 | 0 |
| | No. animals surviving after 11 days | 6 | 3 | 5 | 5 | 3 | 4 | 1½ |
| Mother liquor from recrystallizing amantadine | Survivors | 3 | 3 | 4 | 4 | 6 | 1 | 0 |
| | No. animals surviving when 100% of controls are dead | 3 | 3 | 4 | 4 | 6 | 1 | 0 |
| | No. animals surviving after 11 days | 4 | 4 | 5 | 7 | 7 | 1 | 1½ |

When the compounds of this invention are employed as described above, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay and so forth. They may be administered sublingually in the form of troches or lozenges in which the active ingredient is mixed with sugar and corn syrups; and then dehydrated sufficiently to make it suitable for pressing into a solid form. They may be administered orally in the form of solutions or they may be injected parenterally, that is intramuscularly, intravenously or subcutaneously. For parenteral administration they may be used in the form of a sterile solution containing other solutes, for example, enough saline or glucose to make the solution isotonic.

The dosage of the present pharmacological agents will vary with the form of administration and the particular compound chosen. Furthermore, it will vary with the particular subject under treatment. In general, the compounds of this invention are most desirably administered at a concentration level that will generally afford effective results without causing any harmful or deleterious side effects. For example, the unit dosage quantities of a dosage form for administration to a 60 kilogram host may range from 250 picograms to 15 milligrams.

A solid oral dose form may be prepared as follows:

A predetermined weight of a comminuted compound of this invention is intimately mixed with predetermined amounts of extenders, lubricants, flavoring and the like. The mixture is then subjected to sufficient pressure to form a medicinal tablet for oral medication.

A general tablet formula is:

| Compound of the present invention | 15 ng to 15 mg |
|---|---|
| Extenders, lubricants, flavoring and the like | 50 to 800 mg |
| A particular tablet formula is: | |
| Hydrazine hydrochloride | 12 mg |
| Propanol | 40 mg |
| Mannitol N.F. | 150 mg |
| Starch U.S.P. | 19 mg |
| Sucrose | 2.7 mg |
| Magnesium stearate U.S.P. | 4.0 mg |
| Granulated milk sugar | 220 mg |

To prepare an injectable dose form a predetermined weight of a comminuted compound of the present invention is dissolved in distilled water along with pharmaceutically acceptable compounds to render the solution isotonic. The solution is then filled into a disposable cartridge for use with a syringe for use as dosage form for parenteral administration.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. For instance, the pharmaceutically acceptable acid addition salts of the compounds may be substituted one for the other or for the compound itself.

Without wishing to be bound by a theory of operation it is postulated that the activity of compounds may be due to the alpha effect. The alpha effect is a phenomenon that has been observed in which two electronegative atoms that are adjacent may react with a carboxylic acid group much more strongly than would be predicted from the actual basicity of the compounds. It appears that two electronegative atoms adjacent are essential for the augmentation of reactivity, but not all compounds with two electronegative atoms show equally pronounced alpha effects. It has been found that some compounds having a nitrogen-oxygen bond are active in the practice of this invention, for example, N-hydroxyphthalamide and phenylglyoxaloxime.

What is claimed is:

1. A method of controlling a virus infection in a host suffering from a virus infection in which the virus is a member of the class consisting of Herpes simplex, Vaccinia, Influenza A (PR8), Influenza $A_1$ (Ann Arbor), Influenza $A_2$ (Taiwan), Influenza B (Mass.), Influenza B (Maryland), Mengo, Columbia SK polio, and Neurovaccinio comprising orally administering to the animal host from 250 picograms to 250 micrograms per kilogram of host body weight of a compound is selected from the class consisting of:
   A. 2-Butanone, thiosemicarbazone
   B. 3-Pentanone, thiosemicarbazone
   C. 2-Pentanone, thiosemicarbazone
   D. Acetone, thiosemicarbazone
   E. Acetoacetic acid, ethylester, thiosemicarbazone
   F. Cyclohexanone, thiosemicarbazone
   G. Cyclobutanone, thiosemicarbazone
   H. 2-Indanone, thiosemicarbazone
   I. 2-Indanone, 4-allythiosemicarbazone
   J. Cyclopentanone, o-tolylthiosemicarbazone
   K. Adamantyl thiosemicarbazide
   L. Thiosemicarbazide
   M. Methisazone
   N. Semicarbazide
and the pharmaceutically acceptable acid addition salts thereof.

2. A method as defined in claim 1 in which the compound is administered orally.

3. A method as defined in claim 1 in which the compound is administered in the form of a tablet, capsule or solution.

4. A method as defined in claim 1 in which the compound is administered at 48 hour intervals.

5. A method as defined in claim 1 in which the compound is administered either before or after infection or both before and after infection.

6. A method of controlling a virus infection in a host suffering from a virus infection in which the virus is selected from the group consisting of Herpes simplex, Vaccinia, Influenza A (PR8), Influenza $A_1$ (Ann Arbor), Influenza $A_2$ (Taiwan), Influenza B (Mass.), Influenza B (Maryland), Mengo, Columbia SK polio, and Neurovaccinio comprising orally administering to the animal host from 250 picograms to 250 micrograms per kilogram of host body weight of a compound selected from the group consisting of:
   A. 2-Butanone, thiosemicarbazone
   B. 3-Pentanone, thiosemicarbazone
   C. 2-Pentanone, thiosemicarbazone
   D. Acetone, thiosemicarbazone
   E. Cyclohexanone, thiosemicarbazone
   F. Cyclobutanone, thiosemicarbazone
   G. Cyclopentanone, o-tolylthiosemicarbazone
and the pharmaceutically acceptable acid addition salts thereof.

7. A method as defined in claim 6 in which the compound is administered orally.

8. A method as defined in claim 6 in which the compound is administered in the form of a tablet, capsule or solution.

9. A method as defined in claim 6 in which the compound is administered at 48 hour intervals.

10. A method as defined in claim 6 in which the compound is administered either before or after infection or both before and after infection.

* * * * *